United States Patent
Nagare et al.

(10) Patent No.: US 8,030,267 B2
(45) Date of Patent: Oct. 4, 2011

(54) SILICA COMPOSITE CAPSULES OBTAINED BY BLENDING WATER-SOLUBLE SILANE DERIVATIVE, COMPOSITION CONTAINING THE SAME, AND TRANSPARENT GEL-FORM COMPOSITION

(75) Inventors: Yuko Nagare, Yokohama (JP); Kei Watanabe, Yokohama (JP); Kazutami Sakamoto, Yokohama (JP); Shun Takahashi, Yokohama (JP); Teruhiko Hineno, Yokohama (JP)

(73) Assignee: Shiseido Company Ltd., Chuo-ku, Tokyo (JP)

( * ) Notice: Subject to any disclaimer, the term of this patent is extended or adjusted under 35 U.S.C. 154(b) by 117 days.

(21) Appl. No.: 12/440,614

(22) PCT Filed: Sep. 11, 2007

(86) PCT No.: PCT/JP2007/067653
§ 371 (c)(1),
(2), (4) Date: Mar. 10, 2009

(87) PCT Pub. No.: WO2008/032703
PCT Pub. Date: Mar. 20, 2008

(65) Prior Publication Data
US 2010/0016200 A1    Jan. 21, 2010

(30) Foreign Application Priority Data
Sep. 11, 2006  (JP) .................................. 2006-245798
Sep. 11, 2006  (JP) .................................. 2006-245799

(51) Int. Cl.
*C11D 9/36* (2006.01)
*C11D 3/44* (2006.01)

(52) U.S. Cl. ........ 510/417; 510/122; 510/130; 510/251; 510/343; 510/432; 510/466

(58) Field of Classification Search .................. 510/122, 510/130, 251, 343, 417, 432, 466
See application file for complete search history.

(56) References Cited

U.S. PATENT DOCUMENTS

| 4,476,282 | A * | 10/1984 | Koerner et al. ................ 524/837 |
| 5,306,341 | A * | 4/1994 | Ono et al. ................ 106/287.13 |
| 6,303,149 | B1 * | 10/2001 | Magdassi et al. ............. 424/489 |
| 6,323,268 | B1 * | 11/2001 | Fisher et al. ................. 524/266 |
| 6,403,163 | B1 * | 6/2002 | Fisher et al. ................. 427/387 |
| 6,846,780 | B2 * | 1/2005 | Giraud et al. ................. 508/201 |
| 7,754,776 | B2 * | 7/2010 | Schneider et al. ............. 516/55 |
| 2003/0141015 | A1 * | 7/2003 | Ono ............................... 156/344 |
| 2005/0008600 | A1 * | 1/2005 | Nakanishi et al. .......... 424/70.12 |
| 2005/0084467 | A1 * | 4/2005 | Miyanaga .................. 424/70.12 |
| 2005/0261133 | A1 * | 11/2005 | Nakanishi et al. ............ 504/358 |
| 2006/0034875 | A1 * | 2/2006 | Nakanishi et al. ............ 424/401 |
| 2006/0210506 | A1 * | 9/2006 | Kamei et al. ................ 424/70.7 |
| 2007/0207484 | A1 * | 9/2007 | Brook et al. ...................... 435/6 |

FOREIGN PATENT DOCUMENTS

| JP | 10-218723 | 8/1998 |
| JP | 2001-38193 | 2/2001 |
| JP | 2004-339242 | 12/2004 |

OTHER PUBLICATIONS

Japanese Patent Abstract Publication No. 10-218723 published Aug. 18, 1998, six pages.
Japanese Patent Abstract Publication No. 2004-339242 published Dec. 2, 2004, seven pages.
Japanese Patent Abstract Publication No. 2001-038193 published Feb. 13, 2001, 11 pages.
Sattler et al., "Influence of Surfactant on the Gelation of Novel Ethylene Glycol Esters of Silicic Acid," Ber. Bursenges. Phys. Chem. 102, pp. 1544-1547 (1998) No. 11.
Meyer et al., "Novel Ringing Silica Gels That Do Not Shrink," J. Phys. Chem. B 2002, vol. 106, pp. 1528-1533.
Shchipunov, "Sol-gel-derived biomaterials of silica and carrageenans," Journal of Colloid and Interface Science, vol. 268 (2003) pp. 68-76.
Shchipunov et al., "A new precursor for the immbolization of enzymes inside sol-gel-derived hybrid silica nanocomposites containing polysaccharides," J. Biochem. Biophys. Methods 58 (2004) pp. 25-38.
International Search Report for PCT/JP2007/067653 mailed Dec. 18, 2007, two pages.

* cited by examiner

*Primary Examiner* — Charles Boyer
(74) *Attorney, Agent, or Firm* — Rankin, Hill & Clark LLP

(57) ABSTRACT

The present invention provides new silica composite capsules that can be easily prepared, a composition containing the silica composite capsules, and a transparent gel-form composition excellent in appearance transparency and texture in use, and in particular, a transparent gel-form composition with improved cleansing properties when used as a cleanser. Micelle/silica composite capsules can easily be obtained, in an aqueous system, by mixing a material capable of forming micelles in water and a water-soluble silane derivative having a specific structure in aqueous solution. In addition, emulsion/silica composite capsules wherein the periphery of emulsion particles in the inner phase is coated with silica, can easily be obtained by mixing a surfactant, water, an oil, and a water-soluble silane derivative having a specific structure. Moreover, a transparent gel-form composition showing excellent appearance transparency, the texture in use and cleansing properties, can be obtained by blending a water-soluble silane derivative having a specific structure into the formulation that contains a surfactant, an oil and water, and capable of taking a surfactant association structure with aqueous continuous phase or both of aqueous continuous phase and oil continuous phase in the formulation.

20 Claims, 12 Drawing Sheets

SILICA COMPOSITE CAPSULES OBTAINED BY BLENDING WATER-SOLUBLE SILANE DERIVATIVE, COMPOSITION CONTAINING THE SAME, AND TRANSPARENT GEL-FORM COMPOSITION

RELATED APPLICATIONS

This application claims the priority of Japanese Patent Application No. 2006-245798 and Japanese Patent Application No. 2006-245799 filed on Sep. 11, 2006, which are incorporated herein by reference.

FIELD OF THE INVENTION

The present invention relates to silica composite capsules that can be obtained by blending a water-soluble silane derivative and the composition containing the same, and in particular, relates to the simplification of the production method of silica composite capsules and the preparation of the composition containing the silica composite capsules. In addition, the present invention relates to a transparent gel-form composition that can be obtained by blending a water-soluble silane derivative, and more precisely, relates to a transparent gel-form composition having a specific surfactant association structure and excellent in appearance transparency, texture in use, and cleansing properties.

BACKGROUND OF THE INVENTION

The investigation concerning microcapsules, wherein a core material is contained inside the capsule, has been conducted in various fields such as in recording/display materials, drug delivery systems (DDS), cosmetics/perfume, food products, and agricultural chemicals. In one such example, an attempt was made to improve the drug stability in the product by enclosing the drug inside a capsule.

As such a microcapsule, a silica microcapsule has been known. There have been numerous reports concerning the production methods of silica microcapsules, for example, phase separation method, drying-in-liquid method, spray drying method, interfacial polymerization method, and in-situ polymerization method. However, in order to obtain silica microcapsules containing a core material, a separate treatment such as the impregnation, in a solution wherein the core material has been beforehand dissolved, of hollow silica microcapsules is usually necessary.

On the other hand, a one-step preparation method of the silica composite microcapsules containing a core material has been reported (for example, refer to patent literature 1). The preparation is done by the polymerization of silica, at the water-oil interface, using a water-in-oil type (W/O type) emulsion wherein the aqueous phase containing the core material is dispersed. In this method, however, a water-insoluble tetraalkoxysilane is used; thus the reaction system needs to be a water-in-oil type (W/O type). Therefore, there was a disadvantage in that the form of the obtained formulation is restricted.

In cosmetics and pharmaceuticals, various thickening agents and gelling agents have been used in order to maintain product forms. In the past, as water-based thickening/gelling agents, for example, natural water-soluble polymers such as agar and gelatin and synthetic water-soluble polymers such as polyethylene glycol and acrylic acid polymers were suitably selected and used depending upon respective purposes and effectiveness. However, when the base material was solidified with the use of these water-soluble polymers, there were usability problems in that the skin compatibility was poor or the spreadability during application was poor. In addition, when used as cleansers for cleansing, satisfactory cleansing power could not be obtained.

On the other hand, alkoxysilanes such as tetraethoxysilane are known to form silanol groups by the hydrolysis of alkoxy groups and to form silica gel by their subsequent dehydration-condensation. However, most of conventionally used alkoxysilanes are insoluble in water, and the hydrolysis reaction does not automatically proceed when an alkoxysilane is added into water. Thus, it is necessary to add other additives, and alkoxysilanes are not suitable for the gelation of an aqueous base material. In recent years, a simply mixed aqueous solution of a water-soluble polyhydric alcohol-substituted silane derivative was found to form a solid monolithic silica gel. For example, the application to a silica gel precursor for chromatography or the application to a biosensor, on which a biological component such as an enzyme is immobilized, is reported (for example, refer to patent literature 2 and non-patent literatures 1 to 4). However, the use of such a polyhydric alcohol-substituted silane derivative has not been tried as an aqueous gelling agent.

[Patent Literature 1] Japanese unexamined patent publication No. 2001-38193
[Patent Literature 2] PCT international publication No. WO03/102001
[Non-patent Literature 1] Sattler et al., Ber. Bunsenges. Phys. Chem., 1998, 102, 1544-1547.
[Non-patent Literature 2] Mayer et al., J. Phys. Chem. B, 2002, 106, 1528-1533.
[Non-patent Literature 3] Schipunov, J. Colloid and Interface Sci., 2003, 268, 68-76.
[Non-patent Literature 4] Schipunov et al., J. Biochem. Biophys. Methods, 2004, 58, 25-38.

DISCLOSURE OF THE INVENTION

Problem to be Solved by the Invention

The present invention was made in view of the above-described problem of the conventional art, and a first object is to provide new silica composite capsules that can be easily prepared and a composition containing the silica composite capsule. A second object of the present invention is to provide a transparent gel-form composition excellent in appearance transparency and texture in use, and in particular, a transparent gel-form composition with improved cleansing properties when used as a cleanser.

Means to Solve the Problem

The present inventors have diligently studied in view of the above-described problem of the conventional art. As a result, the present inventors have found that micelle/silica composite capsules can easily be obtained, in an aqueous system, by mixing a material capable of forming micelles in water and a water-soluble silane derivative having a specific structure in aqueous solution and that the thus obtained water-based composition is transparent and the appearance of the composition is also excellent. In addition, the present inventors have also found that emulsion/silica composite capsules, wherein the periphery of emulsion particles in the inner phase is coated with silica, can easily be obtained by mixing a surfactant, water, an oil, and a water-soluble silane derivative having a specific structure.

In addition, the present inventors have found that a transparent gel-form composition having a surfactant association structure with aqueous continuous phase or both of aqueous continuous phase and oil continuous phase, can be obtained by blending a water-soluble silane derivative having a specific structure into the formulation that can take a surfactant association structure with aqueous continuous phase or both of aqueous continuous phase and oil continuous phase, through the solidification of the aqueous phase by the hydrolysis and dehydration condensation reaction in water. In addition, the present inventors have found that the thus obtained transparent gel-form composition has excellent appearance transparency and a specific surfactant association structure and that the skin compatibility is good and the texture in use such as spreadability during application is excellent because the gel easily disintegrates during use. Furthermore, the present inventors have found that silica gel and a polyhydric alcohol are formed, in the formulation, during the solidification reaction of the water-soluble silane derivative. Thus, the present inventors have found that not only the appearance transparency and the texture in use are excellent but also the transparent gel-form cleansers with excellent cleansing properties can be obtained; thus leading to completion of the present invention.

That is, the micelle/silica composite capsule of the present invention is characterized by comprising a micelle that consists of a material capable of forming micelles in water, wherein the outer periphery of the micelle is coated with silica.

In addition, the production method of the micelle/silica composite capsule of the present invention is characterized by comprising the step of mixing a material capable of forming micelles in water and a water-soluble silane derivative represented by the below-described general formula (1), in an aqueous solution.

$$Si—(OR^1)_4 \quad (1)$$

In the formula, at least one of $R^1$s is a polyhydric alcohol residue and the rest can be alkyl groups.

In addition, the water-based transparent composition of the present invention is characterized by comprising the micelle/silica composite capsule which is dispersed in the aqueous phase.

In addition, the water-based transparent cosmetic of the present invention is characterized by consisting of the water-based transparent composition.

The emulsion/silica composite capsule of the present invention is characterized by comprising an emulsion particle that consists of a surfactant and water or an oil, wherein the outer periphery of the emulsion particle is coated with silica.

In addition, the production method of the emulsion/silica composite capsule of the present invention is characterized by comprising the step of mixing a surfactant, water, an oil and a water-soluble silane derivative represented by the below-described general formula (1).

$$Si—(OR^1)_4 \quad (1)$$

In the formula, at least one of $R^1$s is a polyhydric alcohol residue and the rest can be alkyl groups.

In addition, the emulsion composition of the present invention is characterized by comprising the emulsion/silica composite capsule which is emulsified and dispersed in the outer phase.

In addition, the emulsion cosmetic of the present invention is characterized by consisting of the emulsion composition The transparent gel-form composition of the present invention is characterized by being obtained by blending a water-soluble silane derivative represented by the below-described general formula (1) into the formulation that contain a surfactant, water, and an oil, and characterized by having a surfactant association structure with aqueous continuous phase or both of aqueous continuous phase and oil continuous phase in the composition.

$$Si—(OR^1)_4 \quad (1)$$

In the formula, at least one of $R^1$s is a polyhydric alcohol residue and the rest can be alkyl groups.

In addition, in the transparent gel-form composition, it is preferable that a water-soluble compound having hydroxyl groups is also contained in the formulation.

In addition, in the transparent gel-form composition, it is preferable that a lamellar phase structure or bicontinuous phase structure is taken.

In addition, in the transparent gel-form composition, it is preferable that a lamellar phase structure is taken.

In addition, in the transparent gel-form composition, it is preferable that the blending quantity of the surfactant is 20 mass % or higher of the total composition.

In addition, in the transparent gel-form composition, it is preferable that the blending ratio of the water-soluble silane derivative and the surfactant (water-soluble silane derivative/surfactant) is 0.5 or lower.

In addition, in the transparent gel-form composition, it is preferable that the surfactant is a nonionic surfactant.

In addition, in the transparent gel-form composition, it is preferable that at least one surfactant is a polyoxyethylene glycerin fatty acid ester.

In addition, in the transparent gel-form composition, it is preferable that at least one oil component is a silicone oil.

In addition, in the transparent gel-form composition, it is preferable that at least one water-soluble compound having hydroxyl groups is ethanol, glycerin, or 1,3-butylene glycol.

The transparent gel-form cosmetic of the present invention is characterized by consisting of the transparent gel-form composition.

In addition, the transparent gel-form cleanser of the present invention is characterized by consisting of the transparent gel-form composition.

In addition, the production method of the transparent gel-form composition of the present invention is characterized by comprising the step of blending a water-soluble silane derivative represented by the below-described general formula (1) into the formulation that contains a surfactant, an oil and water, and capable of taking a surfactant association structure with aqueous continuous phase or both of aqueous continuous phase and oil continuous phase in the formulation.

$$Si—(OR^1)_4 \quad (1)$$

In the formula, at least one of $R^1$s is a polyhydric alcohol residue and the rest can be alkyl groups.

Effect of the Invention

According to the present invention, micelle/silica composite capsules can be easily obtained, in an aqueous system, by mixing a material capable of forming micelles in water and a water-soluble silane derivative having a specific structure in aqueous solution. The thus obtained water-based composition is transparent, and the appearance of the composition is also excellent. In addition, according to the present invention, emulsion/silica composite capsules wherein the periphery of emulsion particles in the inner phase is coated with silica can easily be obtained by mixing a surfactant, water, an oil, and a water-soluble silane derivative having a specific structure.

In addition, according to the present invention, a transparent gel-form composition can be obtained by blending a water-soluble silane derivative having a specific structure into the formulation that can take a surfactant association structure with aqueous continuous phase or both of aqueous continuous phase and oil continuous phase. The thus obtained transparent gel-form composition is excellent in appearance transparency and has a surfactant association structure with aqueous continuous phase or both of aqueous continuous phase and oil continuous phase. Because the gel easily disintegrates during use, the skin compatibility is good, the texture in use such as spreadability during application is good, and the cleansing properties are also excellent when used as cleansers.

BEST MODE FOR CARRYING OUT THE INVENTION

Micelle/Silica Composite Capsules

Figure 1:
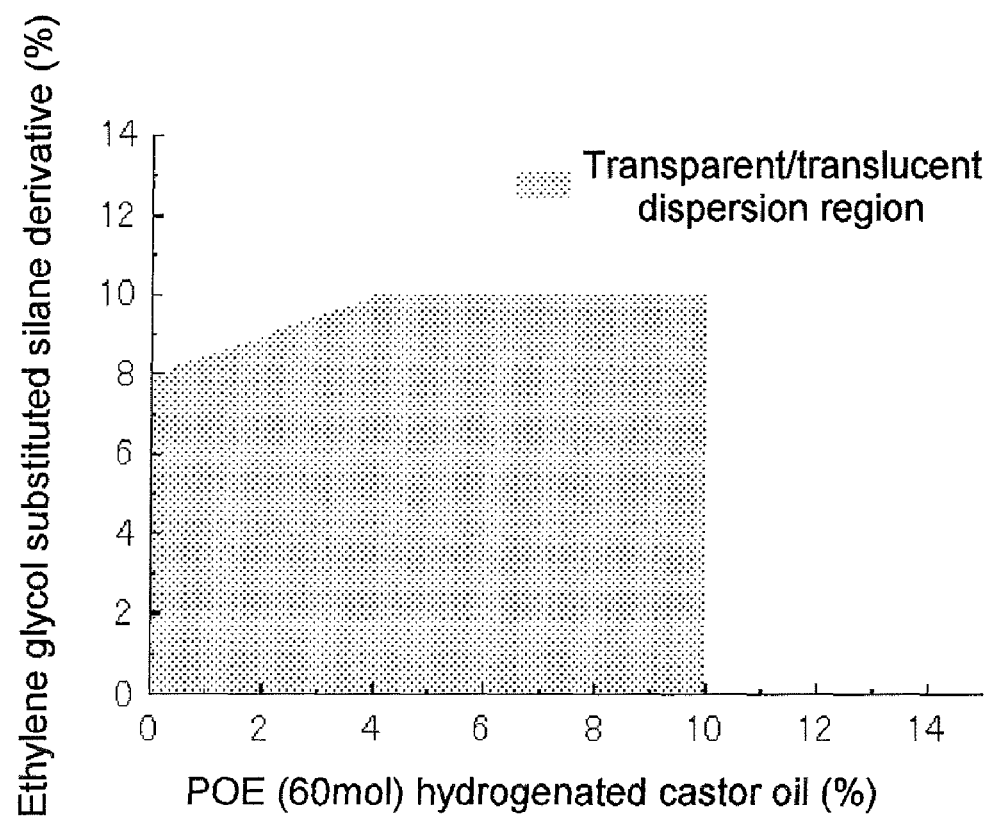
FIG. 1 summarizes the results of observed states of the obtained compositions when the respective concentrations of polyoxyethylene hydrogenated castor oil/ethylene glycol-substituted silane derivative were varied in aqueous solution.
Figure 2:
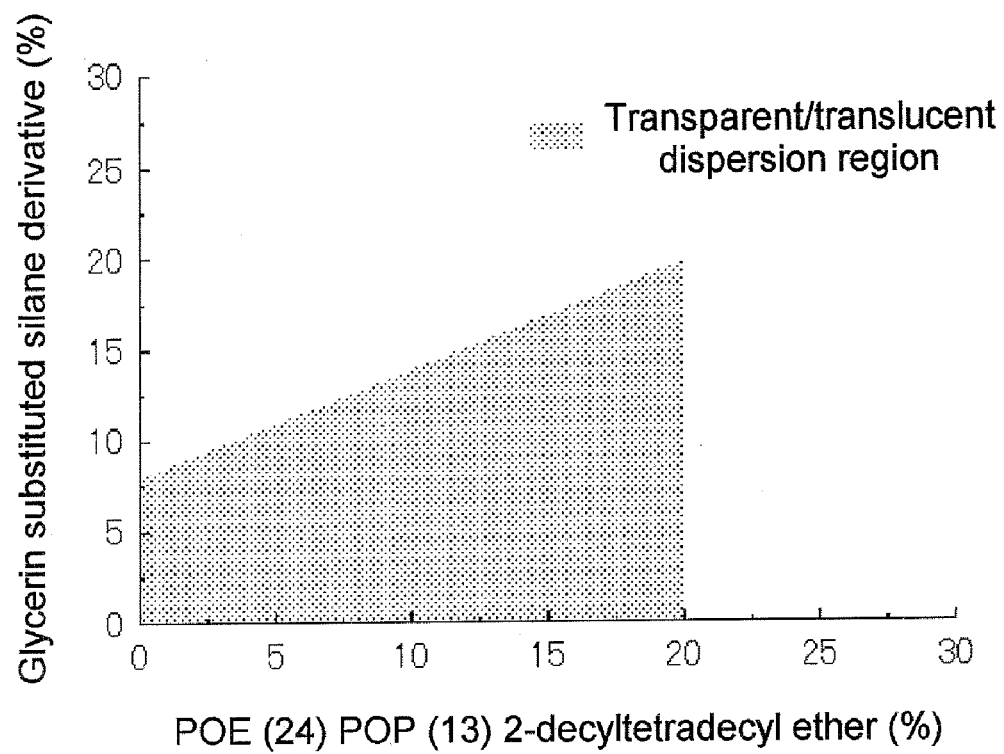
FIG. 2 summarizes the results of observed states of the obtained compositions when the respective concentrations of polyoxyethylene (24 mol) polyoxypropylene (13 mol) 2-decyltetradecyl ether/glycerin-substituted silane derivative were varied in aqueous solution.
Figure 3:
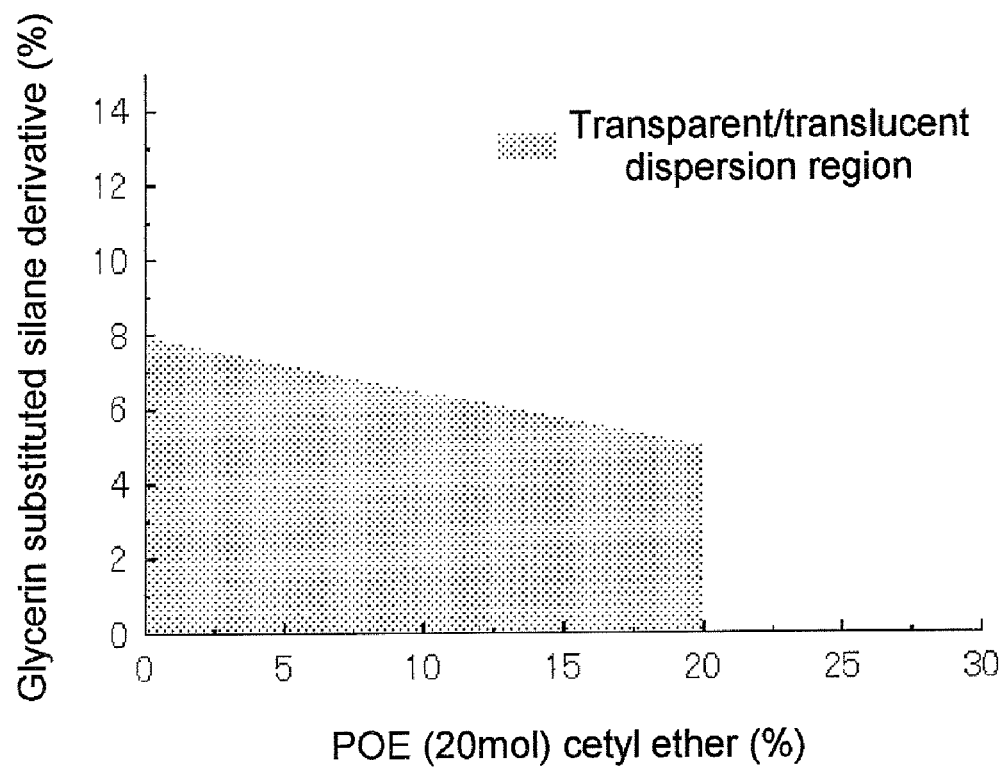
FIG. 3 summarizes the results of observed states of the obtained compositions when the respective concentrations of polyoxyethylene (20 mol) cetyl ether/glycerin-substituted silane derivative were varied in aqueous solution.
Figure 4:
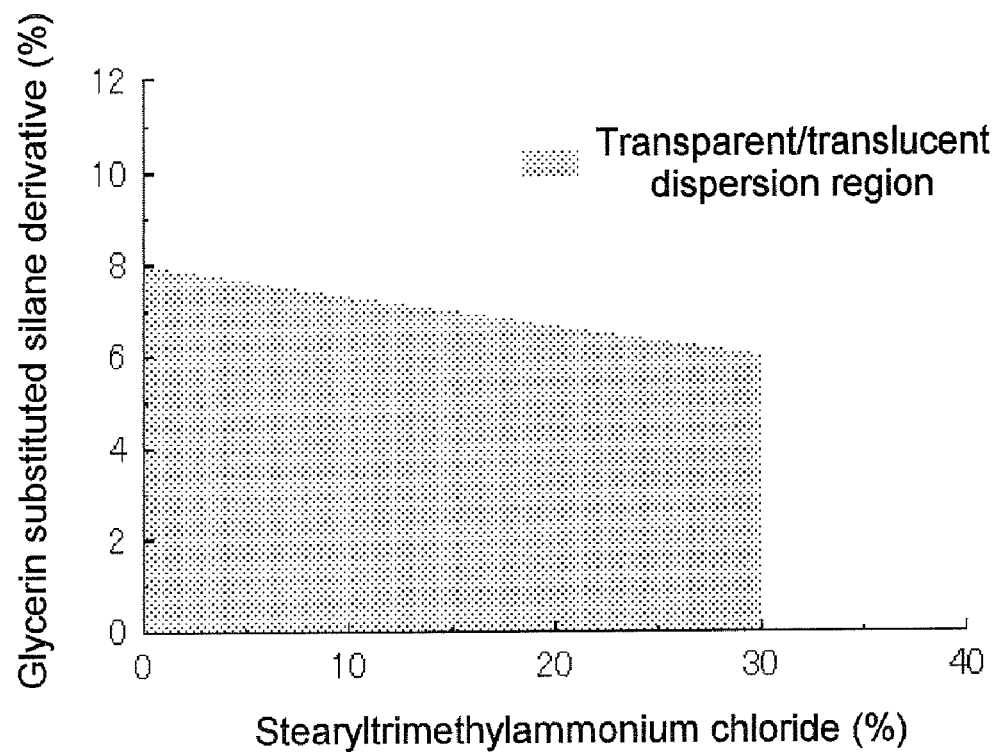
FIG. 4 summarizes the results of observed states of the obtained compositions when the respective concentrations of sodium polyoxyethylene (2 mol) lauryl ether carboxylate/glycerin-substituted silane derivative were varied in aqueous solution.
Figure 5:
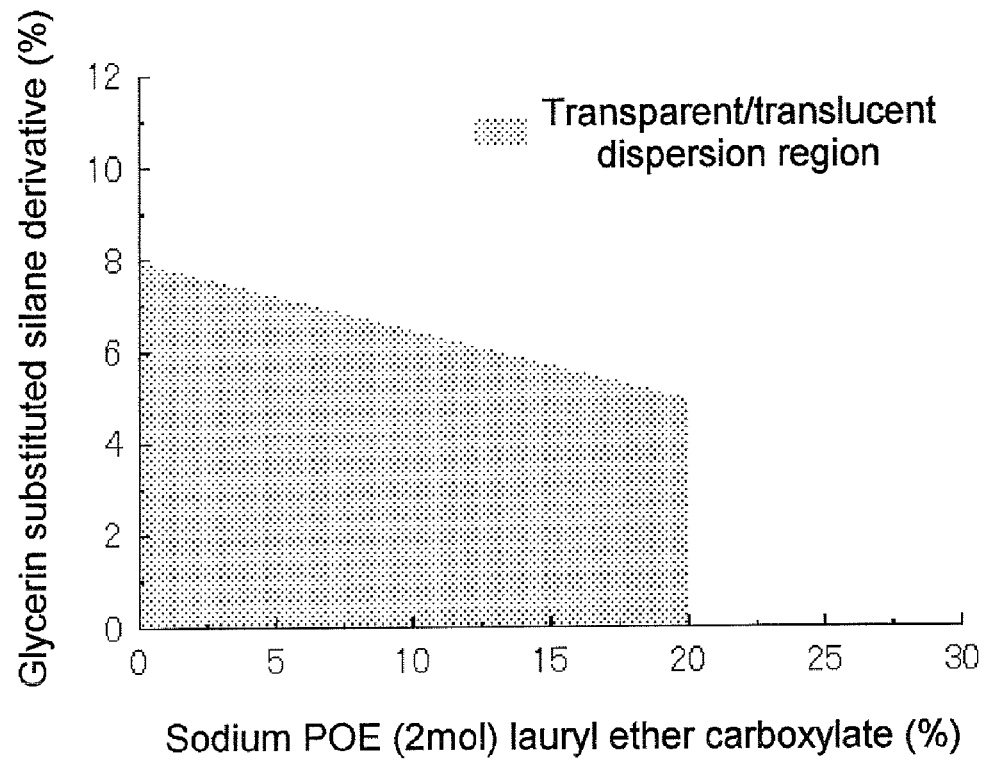
FIG. 5 summarizes the results of observed states of the obtained compositions when the respective concentrations of stearyltrimethylammonium chloride/glycerin-substituted silane derivative were varied in aqueous solution.
Figure 6:
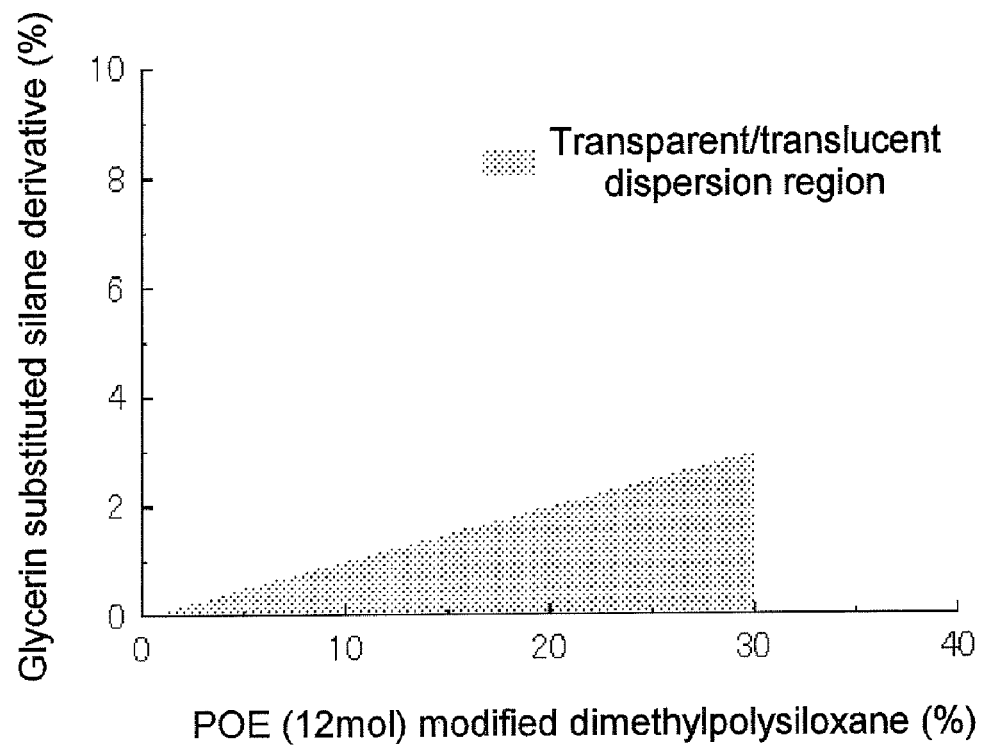
FIG. 6 summarizes the results of observed states of the obtained compositions when the respective concentrations of polyoxyethylene (12 mol)-modified dimethylpolysiloxane/glycerin-substituted silane derivative were varied in aqueous solution.

The micelle/silica composite capsules of the present invention can be obtained by mixing a material capable of forming micelles in water and a water-soluble silane derivative represented by the below-described general formula (1), in aqueous solution.

$$Si-(OR^1)_4 \tag{1}$$

In the formula, at least one of $R^1$s is a polyhydric alcohol residue and the rest can be alkyl groups.

Micelle-Forming Material

The material capable to form micelles in water (hereinafter simply referred to as "micelle-forming material") is not limited in particular, and the representative examples include various surfactants such as anionic surfactants, cationic surfactants, amphoteric surfactants, and nonionic surfactants.

Surfactants

Examples of anionic surfactants include fatty acid soaps (e.g., sodium laurate and sodium palmitate); higher alkyl sulfate ester salts (e.g., sodium lauryl sulfate and potassium lauryl sulfate); alkyl ether sulfate ester salts (e.g., triethanolamine POE-lauryl sulfate and sodium POE-lauryl sulfate); N-acylsarcosinic acids (e.g., sodium lauroylsarcosinate); higher fatty acid amide sulfonate salts (e.g., sodium N-myristoyl-N-methyltaurine, sodium coconut oil fatty acid methyltauride, and sodium laurylmethyltauride); phosphate ester salts (sodium POE-oleyl ether phosphate and POE-stearyl ether phosphate); sulfosuccinate salts (e.g., sodium di-2-ethylhexylsulfosuccinate, sodium monolauroylmonoethanolamide polyoxyethylene sulfosuccinate, and sodium laurylpolypropylene glycol sulfosuccinate); alkylbenzenesulfonate salts (e.g., sodium linear dodecylbenzenesulfonate, triethanolamine linear dodecylbenzenesulfonate, and linear dodecylbenzenesulfonic acid); higher fatty acid ester sulfate ester salts (e.g., sodium hydrogenated coconut oil fatty acid glycerin sulfate); N-acylglutamate salts (e.g., monosodium N-lauroylglutamate, monosodium N-stearoylglutamate, and monosodium N-myristoyl-L-glutamate); sulfated oils (e.g., Turkey red oil); POE-alkyl ether carboxylic acids; POE-alkylallyl ether carboxylic acid salts; α-olefin sulfonate salts; higher fatty acid ester sulfonate salts; secondary alcohol sulfate ester salts; higher fatty acid alkylolamide sulfate ester salts; sodium lauroyl monoethanolamide succinate; ditriethanolamine N-palmitoyl aspartate; and sodium caseinate.

Examples of cationic surfactants include alkyltrimethylammonium salts (e.g., stearyltrimethylammonium chloride and lauryltrimethylammonium chloride); alkylpyridinium salts (e.g., cetylpyridinium chloride); distearyldimethylammonium chloride; dialkyldimethylammonium salts; poly(N,N'-dimethyl-3,5-methylenepiperidinium)chloride; alkyl quaternary ammonium salts; alkyldimethylbenzylammonium salts; alkylisoquinolium salts; dialkylmorpholinium salts; POE-alkylamines; alkylamine salts; polyamine fatty acid derivatives; amyl alcohol fatty acid derivatives; benzalkonium chloride; and benzethonium chloride.

Examples of amphoteric surfactants include imidazoline-based amphoteric surfactants (e.g., sodium 2-undecyl-N,N,N-(hydroxyethylcarboxymethyl)-2-imidazolate and 2-cocoyl-2-imidazoliniumhydroxide-1-carboxyethyloxy disodium salt); and betaine-based surfactants (e.g., 2-heptadecyl-N-carboxymethyl-N-hydroxyethylimidazolinium betaine, lauryldimethylaminoacetate betaine, alkylbetaine, amidobetaine, and sulfobetaine).

Examples of lipophilic nonionic surfactants include sorbitan fatty acid esters (e.g., sorbitan monooleate, sorbitan monoisostearate, sorbitan monolaurate, sorbitan monopalmitate, sorbitan monostearate, sorbitan sesquioleate, sorbitan trioleate, penta-2-ethylhexylic acid diglycerol sorbitan, and tetra-2-ethylhexylic acid diglycerol sorbitan); glycerin polyglycerin fatty acids (e.g., cotton oil fatty acid monoglyceride, glyceryl monoerucate, glyceryl sesquioleate, glyceryl monostearate, glyceryl α,α'-oleate pyroglutamate, and glyceryl monostearate malate); propylene glycol fatty acid esters (e.g., propylene glycol monostearate); hydrogenated castor oil derivatives; and glycerin alkyl ethers.

Examples of hydrophilic nonionic surfactants include POE-sorbitan fatty acid esters (e.g., POE-sorbitan monooleate, POE-sorbitan monostearate, POE-sorbitan monooleate, and POE-sorbitan tetraoleate); POE-sorbitol fatty acid esters (e.g., POE-sorbitol monolaurate, POE-sorbitol monooleate, POE-sorbitol pentaoleate, and POE-sorbitol monostearate); POE-glycerin fatty acid esters (e.g., POE-glycerin monostearate, POE-glycerin monoisostearate, POE-glycerin triisostearate and POE-monooleate); POE-fatty acid esters (e.g., POE-distearate, POE-monodioleate, and ethylene glycol distearate); POE-alkyl ethers (e.g., POE-lauryl ether, POE-oleyl ether, POE-stearyl ether, POE-behenyl ether, POE-2-octyldodecyl ether, and POE-cholesteryl ether, and POE-phytosterol ether); Pluronic types (e.g., Pluronic); POE/POP-alkyl ethers (e.g., POE/POP-cetyl ether, POE/POP-2-decyltetradecyl ether, POE/POP-monobutyl ether, POE/POP-hydrogenated lanolin, and POE/POP-glycerin ether); tetraPOE/tetraPOP-ethylenediamine condensates (e.g., Tetronic); POE-castor oil/hydrogenated castor oil derivatives (e.g., POE-castor oil, POE-hydrogenated castor oil, POE-hydrogenated castor oil monoisostearate, POE-hydrogenated castor oil triisostearate, POE-hydrogenated castor oil monopyroglutamate monoisostearate diester, and POE-hydrogenated castor oil maleate); POE-beeswax/lanolin derivatives (e.g., POE-sorbitol beeswax); alkanol amides (e.g., coconut oil fatty acid diethanolamide, lauric acid monoethanolamide, and fatty acid isopropanolamide); POE-propylene glycol fatty acid esters; POE-alkylamines; POE-fatty acid amides; sucrose fatty acid esters; alkylethoxydimethylamine oxides; and trioleylphosphoric acid.

In the micelle/silica composite capsules of the present invention, nonionic surfactants are preferably used as the micelle-forming-material. Among them, nonionic surfactants having a hydrophilic group with branched chains are especially preferable. A specific example of a hydrophilic group with branched chains includes the polyoxypropylene group. When a nonionic surfactant having a hydrophilic group with branched chains is used, the solidification of the bulk phase is difficult to take place, and it is possible to react with a larger amount of a water-soluble silane derivative compared with, for example, the case wherein a nonionic surfactant having only a linear hydrophilic group such as the polyoxyethylene group is used.

In the micelle/silica composite capsules of the present invention, the above-described micelle-forming material needs to be used at a concentration at which micelles can be formed in aqueous solution and the micelles are transparently dispersible. The concentration at which micelles start to be formed is called the critical micelle concentration (CMC), and it is an intrinsic value specific to each micelle-forming material. For example, there have been numerous reports concerning the critical micelle concentration (CMC) of any given surfactant, and it is available, as needed, for most surfactants.

In addition, the micelle/silica composite capsules of the present invention are allowed to be in a state of swelled micellar solution wherein any given water-insoluble component is solubilized in the micelle. For example, when the micelle-forming material is a surfactant, it is possible to prepare a swelled micellar solution wherein an oil component is solubilized in the surfactant micelle. In this case, micelle/silica composite capsules wherein an oil component is enclosed in the micelle are obtained. As the component of the capsule core, drug, paint, etc. can be suitably selected, depending upon the purpose, for blending.

When any given insoluble component is solubilized in a surfactant, the solubilized system is generally differentiated to be a swelled micellar solution or an emulsion depending upon whether the solubilized system is thermodynamically stable (one-phase system) or unstable (two-phase system). In the present invention, in the same way as the above-described micelle/silica composite capsules, emulsion/silica composite capsules, in which the emulsion is formed with a surfactant, can also be formed.

Emulsion/Silica Composite Capsules

That is, the emulsion/silica composite capsules of the present invention can be obtained by mixing a surfactant, water, an oil, and a water-soluble silane derivative represented by the above-described general formula (1).

As a surfactant for the emulsion/silica composite capsules of the present invention, the above-listed surfactants can be used. As a surfactant, nonionic surfactants are preferably used; among them, nonionic surfactants having a hydrophilic group with branched chains are especially preferable.

The oil component used for the emulsion/silica composite capsules of the present invention is not limited in particular, and oil components used in general cosmetics can be used. Examples include silicone oils, synthetic and natural ester oils, and hydrocarbons. These oil components may be used alone or in combination of two or more.

In the emulsion/silica composite capsules of the present invention, a surfactant, water, and an oil are used, respectively, at a concentration at which the formation of an emulsion is possible. The form of emulsion may be either an O/W emulsion, wherein the oil phase is emulsified and dispersed in the outer aqueous phase, or a W/O emulsion wherein the aqueous phase is emulsified and dispersed in the outer oil phase; however, an O/W emulsion is preferable. In the case of an O/W emulsion, emulsion/silica composite capsules wherein the outer periphery of emulsion particles containing an oil component is coated with silica can be obtained. On the other hand, in the case of a W/O emulsion, emulsion/silica composite capsules wherein the inner periphery of emulsion particles containing an aqueous component is coated with silica can be obtained. Water-based or oil-based drugs, paints, etc. can suitably be blended into these emulsions as a capsule core component.

In the production method of the present invention, the preferable concentration of the above-described micelle-forming material (surfactant) varies depending upon the kinds of micelle-forming materials (surfactants); however, it is preferable to use in the range of 0.1 to 30.0 mass % of the total composition. In order to preferentially expedite the polymerization of silica at the periphery of micelle (emulsion) and prepare silica composite capsules, it is necessary that a certain number of micelles (emulsion particles) are dispersed at a certain distance in aqueous solution. Thus, if the concentration is less than 0.1 mass %, the number of micelles (emulsion particles) in the aqueous solution is too small and an excess of the water-soluble silane derivative polymerizes in the bulk phase, and the entire system may solidify. If the concentration exceeds 30.0 mass %, micelles (emulsion) become too close to each other, and the linking takes place during the silica polymerization process and the formation of a network takes place; as a result, the entire system may solidify.

Water-Soluble Silane Derivatives

Water-soluble silane derivatives are represented by the above-described general formula (1). In the water-soluble silane derivative represented by the above-described general formula (1), at least one of $R^1$s is a polyhydric alcohol residue and the rest can be alkyl groups. The polyhydric alcohol residue is represented in a form wherein one hydroxyl group is removed from a polyhydric alcohol. The water-soluble silane derivative can usually be prepared by a substitution reaction of tetraalkoxysilane with a polyhydric alcohol. The polyhydric alcohol residue R varies depending upon the kinds of polyhydric alcohols. For example, $R^1$ is —$CH_2$—$CH_2$—OH when ethylene glycol is used as the polyhydric alcohol. Furthermore, at least one of $R^1$s may be a substituted polyhydric alcohol residue and the rest can be unsubstituted alkyl groups.

Examples of polyhydric alcohol residues $R^1$ in the above-described general formula (1) include an ethylene glycol residue, a diethylene glycol residue, a triethylene glycol residue, a tetraethylene glycol residue, a polyethylene glycol residue, a propylene glycol residue, a dipropylene glycol residue, a polypropylene glycol residue, a butylene glycol residue, a hexylene glycol residue, a glycerin residue, a diglycerin residue, a polyglycerin residue, a neopentyl glycol residue, a trimethylolpropane residue, a pentaerythritol residue, and a maltitol residue. Among these, it is preferable that $R^1$ is one selected from the group consisting of an ethylene glycol residue, a propylene glycol residue, a butylene glycol residue, and a glycerin residue.

More specific examples of the water-soluble silane derivative used in the present invention include Si—(O—$CH_2$—$CH_2$—OH)$_4$, Si—(O—$CH_2$—$CH_2$—$CH_2$—OH)$_4$, Si—(O—$CH_2$—$CH_2$—CHOH—$CH_3$)$_4$, and Si—(O—$CH_2$—CHOH—$CH_2$—OH)$_4$.

The water-soluble silane derivative used in the present invention can be prepared, for example, by the reaction of a tetraalkoxysilane and a polyhydric alcohol in the presence of a solid catalyst.

The tetraalkoxysilane may be any so far as four alkoxy groups are bonded to a silicon atom, and it is not limited in particular. Examples of tetraalkoxysilanes for the production of water-soluble silicate monomers include tetramethoxysilane, tetraethoxysilane, tetraisopropoxysilane, tetrapropoxysilane, and tetrabutoxysilane. Among these, the use of tetraethoxysilane is the most preferable from the viewpoint of availability and the safety of reaction by-products.

As an alternative compound for the tetraalkoxysilane, a mono-, di-, or trihalogenated alkoxysilane such as monochlorotriethoxysilane, dichlorodimethoxysilane or monobromotriethoxysilane; or a tetrahalogenated silane such as tetrachlorosilane could be used. However, these compounds generate strong acids such as hydrogen chloride and hydrogen bromide during the reaction with a polyhydric alcohol. As a result, the corrosion of the reaction apparatus may take place, and the post-reaction separation and removal are difficult; thus they are not practicable.

The polyhydric alcohol may be any compound so far as two or more hydroxyl groups are contained in the molecule, and it is not limited in particular. Examples of polyhydric alcohols used for the production of water-soluble silicate monomers include ethylene glycol, diethylene glycol, triethylene glycol, tetraethylene glycol, polyethylene glycol, propylene glycol, dipropylene glycol, polypropylene glycol, butylene glycol, hexylene glycol, glycerin, diglycerin, polyglycerin, neopentyl glycol, trimethylolpropane, pentaerythritol, and maltitol. Among these, it is preferable to use one selected from the group of ethylene glycol, propylene glycol, butylene glycol, and glycerin.

The solid catalyst may be any so far as it is a solid catalyst insoluble in raw materials, reaction solvent, and reaction products and it is a solid having active acid points and/or base points for the substituent exchange reaction on the silicon atom. Examples of the solid catalysts used in the present invention include ion exchange resins and various inorganic solid acid/base catalysts.

Examples of ion exchange resins used as the solid catalyst include acidic cation exchange resins and basic anion exchange resins. Examples of matrix resins for these ion exchange resins include styrene-type, acryl-type, and methacryl-type resins. Examples of functional groups with catalyst activity include sulfonic acid, acrylic acid, methacrylic acid, quaternary ammonium, tertiary amine, and primary and secondary polyamines. The matrix structure of ion exchange resin can be selected, depending upon the objectives, from the group consisting of a gel type, a porous type, and a biporous type.

Examples of acidic cation exchange resins include Amberlite IRC76, FPC3500, IRC748, IRB120B Na, IR124 Na, 200CT Na (manufactured by Rohm and Haas Co.), Diaion SK1B, PK208 (manufactured by Mitsubishi Chemical Corporation), Dowex Monosphere 650C, Marathon C, HCR-S, and Marathon MSC (manufactured by Dow Chemical Company). Examples of basic anion exchange resins include Amberlite IRA400J Cl, IRA402BL Cl, IRA410J Cl, IRA411 Cl, IRA458RF Cl, IRA900J Cl, IRA910CT Cl, IRA67, IRA96SB (manufactured by Rohm and Haas Co.), Diaion SA10A, SAF11AL, SAF12A, PAF308L (manufactured by Mitsubishi Chemical Corporation), Dowex Monosphere 550A, Marathon A, Marathon A2, and Marathon MSA (manufactured by Dow Chemical Company).

Inorganic solid acid/base catalysts used as the solid catalyst are not limited in particular. Examples of inorganic solid acid catalysts include single metal oxides such as $Al_2O_3$, $SiO_2$, $ZrO_2$, $TiO_2$, ZnO, MgO, and $Cr_2O_3$; composite metal oxides such as $SiO_2$—$Al_2O_3$, $SiO_2$—$TiO_2$, $SiO_2$—$ZrO_2$, $TiO_2$—$ZrO_2$, ZnO—$Al_2O_3$, $Cr_2O_3$—$Al_2O3$, $SiO_2$—MgO, and ZnO—$SiO_2$; metal sulfates such as $NiSO_4$ and $FeSO_4$; metal phosphates such as $FePO_4$; immobilized sulfuric acid such as $H_2SO_4/SiO_2$; immobilized phosphoric acid such as $H_2PO_4/SiO_2$; immobilized boric acid such as $H_3BO_3/SiO_2$; natural minerals or layered compounds such as activated clay, zeolite, kaolin, and montmorillonite; synthetic zeolite such as $AlPO_4$-zeolite; and heteropolyacids such as $H_3PW_{12}O_{40}.5H_2O$ and $H_3PW_{12}O_{40}$. Examples of solid inorganic base catalysts include single metal oxides such as $Na_2O$, $K_2O$, $Rb_2O$, $Cs_2O$, MgO, CaO, SrO, BaO, $La_2O_3$, $ZrO_3$, and $ThO_3$; metal salts such as $Na_2CO_3$, $K_2CO_3$, $KHCO_3$, $KNaCO_3$, $CaCO_3$, $SrCO_3$, $BaCO_3$, $(NH_4)_2CO_3$, $Na_2WO_4.2H_2O$, and KCN; metal oxide-supported alkali metals such as Na—$Al_2O_3$ and K—$SiO_2$; zeolite-supported alkali metals such as Na-mordenite; and composite metal oxides such as $SiO_2$—MgO, $SiO_2$—CaO, $SiO_2$—SrO, $SiO_2$—ZnO, $SiO_2$—$Al_2O_3$, $SiO_2$—$ThO_2$, $SiO_2$—$TiO_2$, $SiO_2$—$ZrO_2$, $SiO_2$—$MoO_3$, $SiO_2$—WO, $Al_2O_3$—MgO, $Al_2O_3$—$ThO_2$, $Al_2O_3$—$TiO_2$, $Al_2O_3$—$ZrO_2$, $ZrO_2$—ZnO, $ZrO_2$—$TiO_2$, $TiO_2$—MgO, and $ZrO_2$—$SnO_2$.

A solid catalyst can be easily separated, by the treatment such as filtration or decantation, from the products after the completion of the reaction.

In the production of water-soluble silane derivatives, it is not necessary to use a solvent during the reaction; however, various solvents may be used as necessary. The solvent used in the reaction is not limited in particular, and the examples include aromatic hydrocarbons such as benzene, toluene, and xylene; ester, ether, and ketone solvents such as ethyl acetate, methyl acetate, acetone, methyl ethyl ketone, Cellosolve, diethyl ether, and dioxane; polar solvents such as acetonitrile, dimethylformamide, and dimethyl sulfoxide; and halogenated solvents such as chloroform and dichloromethane. In order to suppress the hydrolysis-condensation reaction of a tetraalkoxysilane, which is used as a raw material, it is desirable to dehydrate the solvent in advance. Among these solvents, it is preferable to use acetonitrile, toluene, etc. that can promote the reaction by removing alcohols, such as ethanol, formed as a reaction by-product to the outside of the system by forming an azeotropic mixture.

In the production method of the present invention, the concentration of the above-described water-soluble silane derivative is not limited in particular. However, it is preferable to use the above-described water-soluble silane derivative in the range of 0.1 to 20.0 mass % of the total composition. If the concentration is less than 0.1 mass %, it may not be sufficient to coat the periphery of micelles (emulsion) with silica. If the concentration exceeds 20.0 mass %, the polymerization of silica may take place in the bulk phase and the entire system may solidify.

In the production method of micelle/silica composite capsules of the present invention, the micelle/silica composite capsules, wherein the outer periphery of the micelle formed from a micelle-forming material is coated with silica, can be obtained as a water-based transparent composition that is dispersed in the aqueous phase. The particle size of the micelle/silica composite capsules obtained by the production method of the present invention varies depending upon the kinds of micelle-forming materials; however, the particle size is about 4 to 20 nm. The micelle/silica composite capsules of the present invention can be used, as they are, in the obtained water-based transparent composition. Alternatively, the filtration etc. may be conducted to isolate only the micelle/silica composite capsules before use.

Similarly, in the production method of emulsion/silica composite capsules of the present invention, the emulsion/silica composite capsules wherein the periphery of O/W or W/O emulsion particles is coated with silica, can be obtained as a transparent or white turbid emulsion composition that is emulsified and dispersed in the outer phase. The particle size of the emulsion/silica composite capsules obtained by the production method of the present invention is not limited in particular, and the particle size is normally about 0.1 to 50 μm. The emulsion/silica composite capsules of the present invention can be used, as they are, in the emulsion composition. Alternatively, the filtration etc. may be conducted to isolate only the emulsion/silica composite capsules before use.

In the production method of the present invention, other components in addition to the above-described micelle-forming material (surfactant) and a water-soluble silane derivative, which are essential components, can be blended into the aqueous solution so far as the effect of the present invention is not undermined, namely, in the range that the silica composite capsules of the present invention can be formed. For example, when the water-based transparent composition or emulsion composition obtained by the production method of the present invention is directly used in cosmetics or pharmaceuticals, moisturizers, gelling agents, water-soluble polymers, saccharides, UV absorbers, amino acids, vitamins, drugs, plant extracts, organic acids, organic amines, sequestering agents, antioxidants, antibacterial agents, preservatives, refresheners, perfumes, emollients, pigments, etc., which are normally used as base components or additive components of cosmetics, pharmaceuticals, etc., can be blended. In addition, drugs such as whitening agents, anti-wrinkle agents, anti-aging agents, anti-inflammatory agents, hair growth agents, hair growth-promoting agents, and proteases, which are used to provide functionality to cosmetics, and drug components for external medicine such as anti-inflammatory agents including steroids and nonsteroids, immunosuppressive agents, analgesic-antiinflammatory agents, antibacterial agents, antifungal agents, antiviral agents, antitumor agents, antiulcer-antidecubitus agents, wound dressing agents, circulation improving agents, antipruritic agents, topical anesthetic agents, anti-motion sickness agents, nicotine agents, and female hormonal agents can also be blended. On the other hand, the above-described various components may be beforehand blended into the water-based transparent composition or emulsion composition that is prepared by the production method of the present invention to use them as cosmetics, pharmaceuticals, etc.

In the water-based transparent composition or emulsion composition of the present invention, a polyhydric alcohol, which is formed in the process of the hydrolysis and dehydration condensation of a water-soluble silane derivative, is contained. The polyhydric alcohol varies depending upon the kinds of used water-soluble silane derivatives, and the examples of polyhydric alcohols include ethylene glycol, diethylene glycol, triethylene glycol, tetraethylene glycol, polyethylene glycol, propylene glycol, dipropylene glycol, polypropylene glycol, butylene glycol, hexylene glycol, glycerin, diglycerin, polyglycerin, neopentyl glycol, trimethylolpropane, pentaerythritol, and maltitol. These polyhydric alcohols are widely used in cosmetics, pharmaceuticals, etc., as a moisturizer component etc. The water-based transparent composition or emulsion composition of the present invention has various effects such as moisturizing properties, without blending a special component separately, due to a polyhydric alcohol, which is formed in the process of the polymerization of silica.

In the water-based transparent composition of the present invention, "transparent" means that when the composition is observed from a certain direction, light is transmitted to the extent that the opposite side can be recognized. The water-based transparent composition of the present invention need not be completely colorless; it needs to be transparent only when coloring agents such as dye and pigment are removed. More specifically, the transmittance is at least 5% or higher when a cell with an optical path length of 10 mm is filled and the light transmittance at the wavelength of 550 nm is measured with a spectrophotometer.

The application of the water-based transparent composition or emulsion composition of the present invention is not limited in particular, and they can preferably be used as cosmetics. Thus, the water-based transparent composition or emulsion composition of the present invention can be applied, for example, to cosmetics such as facial cleanser, foundation pre-makeup, essence, milky lotion, cream, and makeup; drug products containing cataplasm or percutaneously absorbable drug; and various other products.

Transparent Gel-Form Composition

In addition, a transparent gel-form composition can be obtained by blending the above-described water-soluble silane derivative having a specific structure into the formulation that can take a surfactant association structure with aqueous continuous phase or both of aqueous continuous phase and oil continuous phase in the formulation. The thus obtained transparent gel-form composition is excellent in appearance transparency and has a surfactant association structure with aqueous continuous phase or both of aqueous continuous phase and oil continuous phase in the composition. Because the gel easily disintegrates during use, the skin compatibility is good, the texture in use such as spreadability during application is good, and the cleansing properties are also excellent when used as cleansers.

Thus, the transparent gel-form composition of the present invention is characterized in that it is obtained by blending a water-soluble silane derivative represented by the below-described general formula (1) into the formulation containing a surfactant, water, and an oil and in that it has a surfactant association structure with aqueous continuous phase or both of aqueous continuous phase and oil continuous phase.

$$Si-(OR^1)_4 \qquad (1)$$

In the formula, at least one of $R^1$s is a polyhydric alcohol residue and the rest can be alkyl groups.

The surfactant used in the transparent gel-form composition of the present invention is not limited in particular so far as a surfactant association structure, which has aqueous continuous phase or both of aqueous continuous phase and oil continuous phase, can be formed. For example, the above-listed surfactants can be used. As the surfactant, a nonionic surfactant is preferably used, and a polyoxyethylene glycerin fatty acid ester is especially preferably used. As the hydrophobic alkyl group, a branched-chain alkyl group is preferable, and especially an isostearic group is preferable. More specific examples include polyoxyethylene (5 to 12 mol) glyceryl monoisostearate.

The surfactant may be used alone or in combination of two or more. The blending quantity of the surfactant is preferably 20 mass % or higher of the total composition, and more preferably 40 to 60 mass %. If the blending quantity is less than 20 mass %, it may be difficult to form a surfactant association structure with aqueous continuous phase or both of aqueous continuous phase and oil continuous phase, and the texture in use such as skin compatibility may be inferior.

The blending quantity of water used in the transparent gel-form composition of the present invention can be suitably set depending upon the application purpose; however, it is especially preferable to be 10 to 60 mass %. In addition, it is preferable that the blending ratio of the surfactant and water (surfactant/water) is 0.5 to 4. If the blending ratio is less than 0.5, the texture in use such as skin compatibility may be inferior. If the blending ratio exceeds 4, stickiness may be caused.

The oil component used in the transparent gel-form composition of the present invention is not limited in particular; for example, silicone oils can be preferably used. Examples of the silicone oils include linear or cyclic polysiloxanes such as dimethylpolysiloxane, methylphenylpolysiloxane, methylhydrogenpolysiloxane, decamethylpolysiloxane, dodecamethylpolysiloxane, tetramethyltetrahydrogenpolysiloxane, cyclotetradimethylsiloxane, and cyclopentadimethylsiloxane. In addition to the above-described silicone oils, the oil components used in general cosmetics may be used. For example, it is possible to blend polar oils such as synthetic or natural ester oils and specific UV absorbers, or nonpolar oils such as liquid paraffins, squalane, isoparaffins, ceresin, petrolatum, microcrystalline wax, and paraffin wax, which are liquid hydrocarbons, semi-solid (grease-like) hydrocarbons, or solid hydrocarbons.

The oil component can be used alone or in combination of two or more. The blending quantity of the oil component varies depending upon the application purpose of the composition; however, it is preferable to be 1 to 60 mass % of the total composition. If the blending quantity is less than 1 mass %, the texture in use such as skin compatibility may not be satisfactory. If the blending quantity exceeds 60 mass %, stickiness may be caused.

Figure 9:
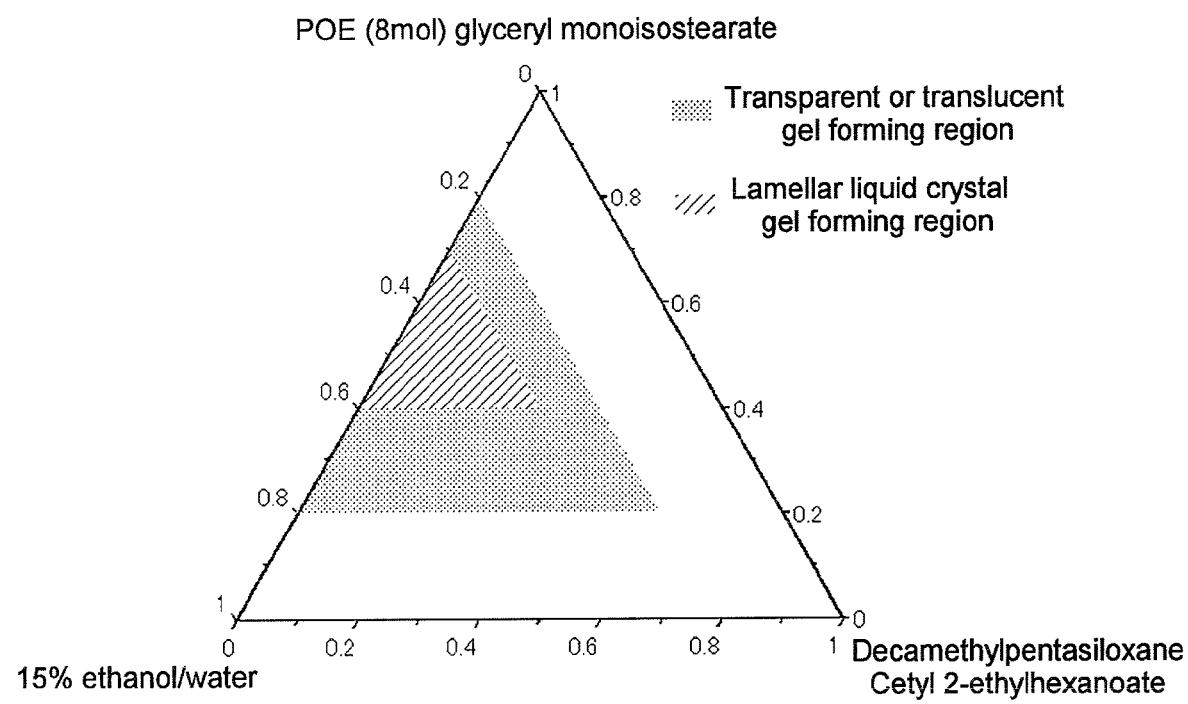
FIG. 9 is a ternary phase diagram that shows the state of the systems when the blending quantity of each component was varied in the composition where polyoxyethylene (8 mol) glyceryl monoisostearate, decamethylcyclopentasiloxane, cetyl 2-ethylhexanoate, water, and ethanol were used.

In the transparent gel-form composition of the present invention, the formulation containing the above-described various components can take a surfactant association structure with aqueous continuous phase or both of aqueous continuous phase and oil continuous phase. It is known that a surfactant association structure with aqueous continuous phase or both of aqueous continuous phase and oil continuous phase, can be taken by the composition containing the above-described various components by adjusting respective quantity ratios to be appropriate or by adding a suitable component separately (for example, a water-soluble compound having hydroxyl groups) (for example, refer to Japanese Unexamined Patent Publication No. 2000-256124). As one example, a ternary phase diagram that shows the state of systems when the blending quantity of each component is varied in the composition wherein polyoxyethylene (8 mol) glyceryl monoisostearate (Emalex GWISS-108: manufactured by Nihon Emulsion Co., Ltd.) as a surfactant, decamethylcyclopentasiloxane (Execol D-5: manufactured by Shin-Etsu Chemical Co., Ltd.) and cetyl 2-ethylhexanoate (Nikkol CIO: manufactured by Nikko Chemicals Co., Ltd.) as oil components, water, and ethanol (special grade: manufactured by Wako Pure Chemical Industries, Ltd.) are used is shown in FIG. 9. In the vicinity of the center, as shown in FIG. 9, there is a triangular region where gels with lamellar liquid crystal structure are formed. On the outer periphery, there is a region where transparent or translucent gels are formed. Here, a surfactant association (bicontinuous phase) structure, which has both of aqueous continuous phase and oil continuous phase, is considered to be formed.

In the transparent gel-form composition of the present invention, a water-soluble silane derivative represented by the above-described general formula (1) is blended into the formulation that contains the above-described various components and can take a surfactant association structure with aqueous continuous phase or both of aqueous continuous phase and oil continuous phase. Thus, silica is formed by hydrolysis and dehydration condensation reaction in water, the aqueous phase, which is a continuous phase of the formulation, is gelated, and a transparent gel-form composition having a surfactant association structure with aqueous continuous phase or both of aqueous continuous phase and oil continuous phase, can be obtained. Examples of such surfactant association structures include a lamellar phase structure and a bicontinuous phase structure. Especially the lamellar phase structure is preferable because excellent cleansing properties can be obtained when used as a cleanser. These surfactant association structures can be identified by a publicly known method such as polarization microscope observation, small-angle X-ray diffraction analysis, or freeze replica electron microscopic observation.

The water-soluble silane derivative used in the transparent gel-form composition of the present invention is represented by the above-described general formula (1). The water-soluble silane derivative can be used alone or in combination of two or more. The blending quantity of the water-soluble silane derivative is not limited in particular; however, it is preferable to be 5 to 60 mass % of the total composition. If the content of the water-soluble silane derivative is less than 5 mass %, a gel-form may not be attained. If the content of the water-soluble silane derivative exceeds 60 mass %, the gel may become too hard and the texture in use may be inferior. In particular, it is preferable that the blending ratio of the water-soluble silane derivative and the surfactant (water-soluble silane derivative/surfactant) is 0.5 or lower.

The water-soluble silane derivative forms silica gel and a polyhydric alcohol by the hydrolysis and dehydration condensation reaction in water. Thus, the aqueous phase is solidified and a transparent gel-form composition with a specific surfactant association structure can be obtained by blending a water-soluble silane derivative into the formulation that can take a surfactant association structure with aqueous continuous phase or both of aqueous continuous phase and oil continuous phase.

The thus obtained transparent gel-form composition of the present invention is excellent in appearance transparency, it has a surfactant association structure with aqueous continuous phase or both of aqueous continuous phase and oil continuous phase, and the gel easily disintegrates during use. Therefore, the transparent gel-form composition of the present invention has good skin compatibility and is excellent in the texture in use such as spreadability during application compared with the case wherein a natural or synthetic water-soluble polymer, which was used as a water-based thickening/gelling agent in the past, is used. Thus, it is desirably used as cosmetics. In addition, silica gel and a polyhydric alcohol are formed, in the formulation, during the solidification reaction of the water-soluble silane derivative. Therefore, when it is used as a cleanser, for example, it is not only excellent in the texture in use but also a transparent gel-form cleanser excellent in cleansing properties can be obtained.

In addition, the transparent gel-form composition of the present invention has a surfactant association structure with aqueous continuous phase or both of aqueous continuous phase and oil continuous phase. Examples of such a surfactant association structure with aqueous continuous phase or both of aqueous continuous phase and oil continuous phase include a lamellar phase structure and a bicontinuous phase structure. Especially the lamellar phase structure is preferable because excellent cleansing properties can be obtained when used as cleansers. These surfactant association structures can be identified by a publicly known method such as polarization microscope observation, small-angle X-ray diffraction analysis, or freeze replica electron microscopic observation.

In the transparent gel-form composition of the present invention, it is preferable to additionally contain a water-soluble compound having hydroxyl groups in the formulation. If a water-soluble compound having hydroxyl groups is contained, a stable surfactant association structure with aqueous continuous phase or both of aqueous continuous phase and oil continuous phase can be easily formed. The water-soluble compound having hydroxyl groups used in the present invention is not limited in particular, and the examples include water-soluble monohydric alcohols and polyhydric alcohols. Examples of water-soluble monohydric alcohols include ethanol, propanol, isopropanol, butanol, and isobutanol. Examples of water-soluble polyhydric alcohols include propylene glycol, 1,3-butylene glycol, dipropylene glycol, glycerin, diglycerin, polyglycerin, erythritol, pentaerythritol, sorbitan, glucose, sorbitol, maltitol, trehalose, and polyethylene glycol. Among these alcohols, ethanol, glycerin, or 1,3-butylene glycol can be especially preferably used.

The water-soluble compound having hydroxyl groups can be used alone or in combination of two or more. The blending quantity of a water-soluble compound having hydroxyl groups varies depending upon viscosity etc. of the intended composition; however, 1 to 30 mass % of the total composition is preferable. If the blending quantity is less than 1 mass %, the texture in use such as skin compatibility may be inferior. If the blending quantity exceeds 30 mass %, undesirable feelings in use such as stickiness and tingling may occur.

In the transparent gel-form composition of the present invention, other components can be suitably blended, as necessary, in addition to the above-described various essential components so far as the effect of the present invention is not undermined. Examples of other components that can be blended include moisturizers, gelling agents other than the above-described water-soluble silane derivatives, water-soluble polymers, saccharides, UV absorbers, amino acids, vitamins, drugs, plant extracts, organic acids, organic amines, sequestering agents, antioxidants, antibacterial agents, preservatives, refresheners, perfumes, emollients, and pigments, which are normally used as base components or additive components of cosmetics, pharmaceuticals, etc. In addition, drugs such as whitening agents, anti-wrinkle agents, anti-aging agents, anti-inflammatory agents, hair growth agents, hair growth-promoting agents, and proteases, which are used to provide functionality to cosmetics, and drug components for external medicine such as anti-inflammatory agents including steroids and nonsteroids, immunosuppressive agents, analgesic-antiinflammatory agents, antibacterial agents, antifungal agents, antiviral agents, antitumor agents, antiulcer-antidecubitus agents, wound dressing agents, circulation improving agents, antipruritic agents, topical anesthetic agents, anti-motion sickness agents, nicotine agents, and female hormonal agents can also be blended.

In the transparent gel-form composition of the present invention, "transparent" means that when the gel-form composition is observed from a certain direction, light is transmitted to the extent that the opposite side can be recognized. The transparent gel-form composition of the present invention need not be completely colorless; it needs to be transparent only when coloring agents such as dye and pigment are removed. More specifically, the transmittance is at least 5% or higher when a cell with an optical path length of 10 mm is filled and the light transmittance at the wavelength of 550 nm is measured with a spectrophotometer.

The application of the transparent gel-form composition of the present invention is not limited in particular, and the transparent gel-form composition of the present invention can preferably be used as cosmetics. In addition, the transparent gel-form composition of the present invention can especially preferably be used as a cleanser. Thus, the transparent gel-form composition of the present invention can be applied, for example, to cleansers such as face cleansing scrub, moisturizing scrub, and enzyme scrub; cosmetics such as foundation pre-makeup, essence, milky lotion, cream, and makeup; drug products containing cataplasm or percutaneously absorbable drug; and various other products.

EXAMPLES

Example 1

Hereinafter, the present invention will be described in further detail with reference to specific examples. However, the present invention is not limited by these examples.

At first, the production method of water-soluble silane derivatives used in the present invention will be explained.

Synthesis Example 1

Ethylene Glycol-Substituted Silane Derivative

To 150 mL of acetonitrile, 20.8 g (0.1 mol) of tetraethoxysilane and 24.9 g (0.4 mol) of ethylene glycol were added, and then 1.8 g of strong acid ion exchange resin (Dowex 50W-X8, manufactured by the Dow Chemical Company) was also added as a solid catalyst. Then the mixture was mixed with stirring at room temperature. The reaction solution, which was initially separated into two layers, became a homogeneous solution after about 1 hour. The stirring of the mixture was continued for 5 days, and then the solid catalyst was separated by filtration. Ethanol and acetonitrile were distilled away under reduced pressure, and 39 g of transparent viscous liquid was obtained. Based on the results of $^1$H-NMR analysis, the product was confirmed to be the desired ethylene glycol substituted compound (tetra(2-hydroxyethoxy)silane) (yield: 72.5%).

Synthesis Example 2

Glycerin-Substituted Silane Derivative

Tetraethoxysilane (60.1 g (0.28 mol)) and glycerin (106.33 g (1.16 mol)) were mixed, and 1.1 g of strong acid ion exchange resin (Dowex 50W-X8, manufactured by the Dow Chemical Company) was added as a solid catalyst. This mixture without a solvent was mixed with stirring at 85° C. After about 3 hours, the mixture became a one-layer transparent solution. After the reaction was continued for an additional 5 hours 30 minutes, the obtained solution was allowed to stand overnight. Under reduced pressure, the solid catalyst was separated by filtration and washed with a small amount of ethanol. From this solution, ethanol was distilled away, and 112 g of transparent viscous liquid was obtained. The product formed a uniform transparent gel, with a slight exotherm, by mixing with the same amount of water at room temperature (yield: 97%).

Micelle/Silica Composite Capsules

The present inventors prepared polyhydric alcohol-substituted water-soluble silane derivatives according to the above-described synthesis examples, mixed various surfactants and the aforementioned water-soluble silane derivatives in aqueous solution, and investigated the obtained compositions. The experiment was as follows. The results are shown in FIGS. 1 to 6.

<Experiment>

Various surfactants and polyhydric alcohol-substituted silane derivatives were used in combinations as shown in the below-described (1) to (6). Respective concentrations were varied, the aqueous solutions were mixed with stirring, and the state of the compositions was visually observed after 4 days.

(1) Surfactant: polyoxyethylene (60 mol) hydrogenated castor oil (Nikkol HCO-60: manufactured by Nikko Chemicals Co., Ltd.)
  Water-soluble silane derivative: ethylene glycol-substituted silane derivative
(2) Surfactant: polyoxyethylene (24 mol) polyoxypropylene (13 mol) 2-decyltetradecyl ether (S-safe 1324 (D): manufactured by Nippon Oil & Fats Co., Ltd.)
  Water-soluble silane derivative: glycerin-substituted silane derivative
(3) Surfactant: polyoxyethylene (20 mol) cetyl ether (Emalex 120: manufactured by Nihon Emulsion Co., Ltd.)
  Water-soluble silane derivative: glycerin-substituted silane derivative
(4) Surfactant: sodium polyoxyethylene (2 mol) lauryl ether carboxylate (AKYPO PLM45NV: manufactured by Nikko Chemicals Co., Ltd.)
  Water-soluble silane derivative: glycerin-substituted silane derivative
(5) Surfactant: stearyltrimethylammonium chloride (Catinal TC-25AQ: manufactured by Toho Chemical Industry, Co., Ltd.)
  Water-soluble silane derivative: glycerin-substituted silane derivative
(6) Surfactant: polyoxyethylene (12 mol)-modified dimethylpolysiloxane*1 (SH3773M: manufactured by Dow Corning Silicone Co., Ltd., HLB=8)
  *1: This is a pendant-type polyoxyalkylene-modified silicone wherein side-chain methyl groups of the linear dimethylpolysiloxane are substituted with polyoxyethylene (12 mol) groups. The percentage of the molecular weight of ethyleneoxide in the total molecular weight is 40%.
  Water-soluble silane derivative: glycerin-substituted silane derivative As shown in FIGS. 1 to 6, it was found that when various surfactants and polyhydric alcohol-substituted water-soluble silane derivatives were mixed in aqueous solution, in the specific concentration range, a transparent or translucent water-based composition, wherein micelle/silica composite capsules were dispersed in the aqueous phase, could be obtained. The polymerization reaction of silica by hydrolysis and dehydration condensation of the water-soluble silane derivative progresses preferentially at the outer periphery of the micelle; as a result, very fine micelle/silica composite capsules are considered to be formed. In addition, it was confirmed that, in each kind of surfactant, nonionic surfactants (1) to (3), anionic surfactant (4), cationic surfactant (5), or silicone surfactant (6), a transparent water-based composition could be obtained though the respective concentration ranges were different.

In addition, the present inventors investigated the particle size change of micelle/silica composite capsules with respect to the added amount of the water-soluble silane derivative with an apparatus for the measurement of particle size distribution that is based on the laser diffraction scattering method. As a surfactant, POE (24 mol) POP (13 mol) 2-decyltetradecyl ether was used, and as a water-soluble silane derivative, a glycerin-substituted silane derivative was used. The test was conducted under the conditions of surfactant concentrations of 5 mass % and 15 mass %, respectively. The results are shown in FIG. 7.

Figure 7:
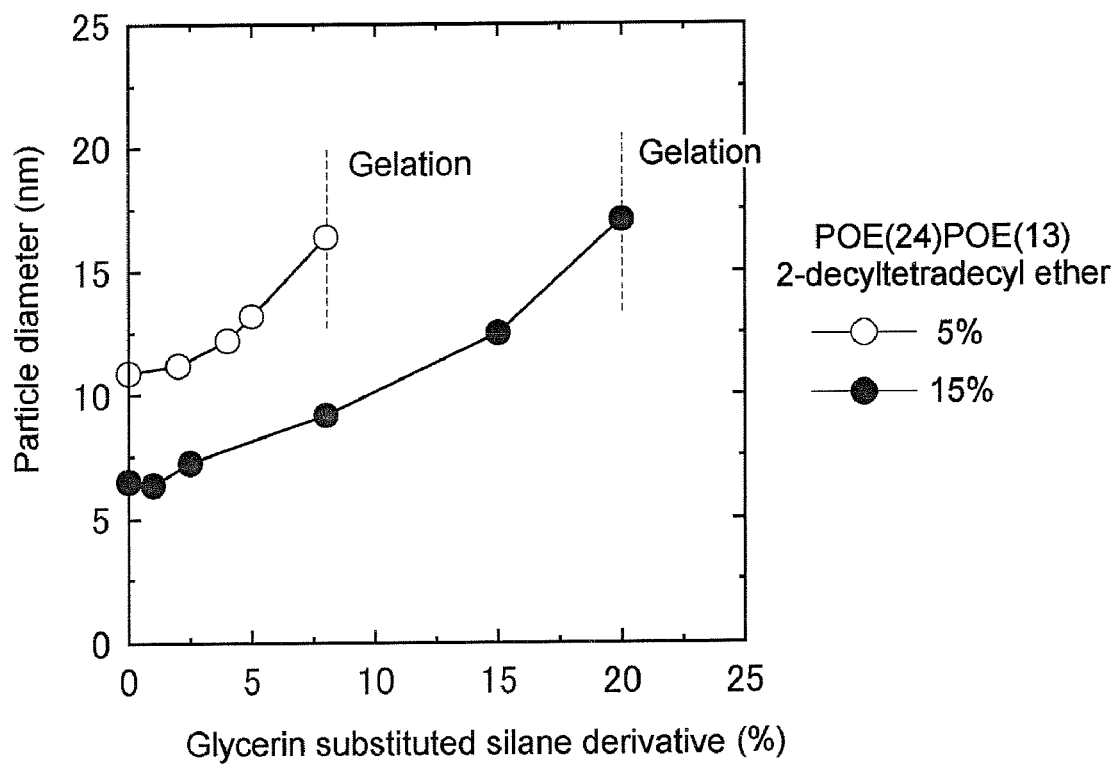
FIG. 7 summarizes the investigation results of the variation of particle size of micelle/silica composite capsules with respect to the amount of the added water-soluble silane derivative, under surfactant concentrations of 5 mass % and 15 mass %, respectively, with the use of POE (24 mol) POP (13 mol) 2-decyltetradecyl ether and a glycerin-substituted silane derivative.

As shown in FIG. 7, when the amount of the added water-soluble silane derivative was varied, the size of particles present in the composition was observed to gradually increase with an increase in the water-soluble silane derivative. Thus, the polymerization of silica progresses at the outer periphery of the micelle that is formed in aqueous solution, and micelle/silica composite capsules, wherein the micelle is coated with silica, are considered to be formed.

Subsequently, the present inventors used different surfactants at the same concentration and investigated the particle size change of micelle/silica composite capsules in the same way as the above-described test. As surfactants, POE (24 mol) POP (13 mol) 2-decyltetradecyl ether and POE (20 mol) cetyl ether were used, and as a water-soluble silane derivative, a glycerin-substituted silane derivative was used. The test was conducted under the condition of a surfactant concentration of 5 mass %. The results are shown in FIG. 8.

Figure 8:
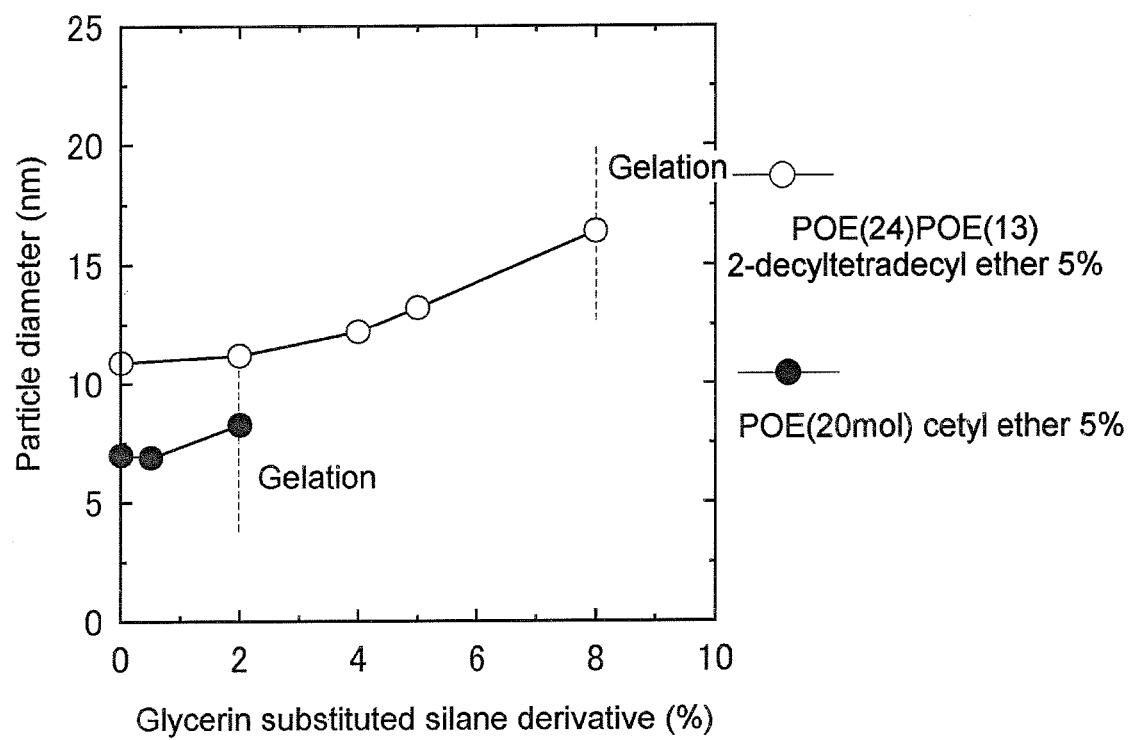
FIG. 8 summarizes the investigation results of the variation of particle size of micelle/silica composite capsules with respect to the amount of the added water-soluble silane derivative, under a surfactant concentration of 5 mass %, with the use of POE (24 mol) POP (13 mol) 2-decyltetradecyl ether or POE (20 mol) cetyl ether and a glycerin-substituted silane derivative.

As shown in FIG. 8, when POE (24 mol) POP (13 mol) 2-decyltetradecyl ether was used, the gelation of the bulk phase did not take place easily compared with the case wherein the same concentration of POE (20 mol) cetyl ether was used, and it was possible to react about 4 times as much water-soluble silane derivative. A micelle in aqueous solution is formed with hydrophilic groups on the exterior; thus the above-described results are deeply related with the structure of surfactant hydrophilic groups. That is, POE (20 mol) POP (13 mol) 2-decyltetradecyl ether has, as the hydrophilic group, a polyoxypropylene group, which has branched chains. It is considered that the polymerization of silica at the outer periphery of a micelle easily progresses because of the presence of this branched chain hydrophilic group.

Thus, it was found that micelle/silica composite capsules could easily be obtained, in an aqueous system, by mixing a surfactant and a water-soluble silane derivative in aqueous solution. The same experiment was also conducted using various surfactants and water-soluble silane derivatives. The particle size of the obtained micelle/silica composite capsules was found to be about 4 to 20 nm.

Emulsion/Silica Composite Capsules

Subsequently, the present inventors tried to prepare silica composite capsules by obtaining an emulsion state after mixing a surfactant, an oil component, and water and then by mixing with a water-soluble silane derivative in the same way as the above-described experiment. The experiment was as follows.

<Experiment>

With a homomixer (manufactured by Tokushu Kika Kogyo Co.), 3 mass % of polyoxyethylene (8 mol) glyceryl monoisostearate (Emalex GWIS-108: manufactured by Nihon Emulsion Co., Ltd.), 10 mass % of glycerin-substituted silane derivative, 5 mass % of decamethylcyclopentasiloxane (Execol D-5: manufactured by Shin-Etsu Chemical Co., Ltd.), 5 mass % of cetyl 2-ethylhexanoate (Nikkol CIO: manufactured by Nikko Chemicals Co., Ltd.), 11 mass % of ethanol (special grade: manufactured by Wako Pure Chemical Industries, Ltd.), and 66 mass % of water were mixed with stirring (9000 rpm, for 90 seconds), and a white turbid O/W emulsion composition was obtained.

In the thus obtained O/W emulsion composition, similarly to the above-described micelle/silica composite capsules, emulsion/silica composite capsules, wherein the O/W emulsion particles are coated with silica, are considered to be formed by the progress of the polymerization of silica at the outer periphery of emulsified and dispersed O/W emulsion particles in the outer aqueous phase.

Example 2

Hereinafter, the present invention will be described in further detail with reference to other examples of the water-based transparent compositions and emulsion compositions of the present invention. However, the present invention is not limited by these examples.

Example 2-1

| Lotion | (mass %) |
| --- | --- |
| Water | 88.045 |
| Glycerin | 2 |
| 1,3-Butylene glycol | 2 |
| Citric acid | 0.02 |
| Sodium citrate | 0.08 |
| EDTA3Na•2H$_2$O | 0.05 |
| Methylparaben | 0.15 |
| Perfume | 0.005 |
| Vitamin E acetate | 0.05 |
| Ascorbic acid glucoside | 2 |
| POE (60 mol) hydrogenated castor oil | 1.6 |
| Ethylene glycol-substituted water-soluble silane derivative | 4 |

Example 2-2

| Lotion | (mass %) |
| --- | --- |
| Water | 88.045 |
| Glycerin | 2 |
| 1,3-Butylene glycol | 2 |
| Citric acid | 0.02 |
| Sodium citrate | 0.08 |
| EDTA3Na•2H$_2$O | 0.05 |
| Methylparaben | 0.15 |
| Perfume | 0.005 |
| Vitamin E acetate | 0.05 |
| Ascorbic acid glucoside | 2 |
| POE (24 mol) POP (13 mol) 2-decyltetradecyl ether | 5 |
| Glycerin-substituted water-soluble silane derivative | 5 |

The obtained lotions in the above-described Examples 2-1 and 2-2 were transparent, and the micelle/silica composite capsule particles were dispersed in the aqueous phase.

Example 2-3

| Milky lotion | (mass %) |
| --- | --- |
| Water | 74.75 |
| POE (20) stearyl ether | 2 |
| Decamethylcyclopentasiloxane | 5 |
| Dimethylsiloxane (6 cs) | 7 |
| Squalane | 5 |
| Glyceryl tri-2-ethylhexanoate | 3 |
| Citric acid | 0.01 |
| Sodium citrate | 0.09 |
| Methylparaben | 0.15 |
| Ethylene glycol-substituted water-soluble silane derivative | 3 |

Example 2-4

| Milky lotion | (mass %) |
| --- | --- |
| Water | 71.25 |
| POE (20) stearyl ether | 2 |
| Decamethylcyclopentasiloxane | 5 |
| Dimethylsiloxane (6 cs) | 7 |
| Squalane | 5 |
| Glyceryl tri-2-ethylhexanoate | 3 |
| Octyl methoxycinnamate | 3 |
| t-Butylmethoxydibenzoylmethane | 0.5 |
| Citric acid | 0.01 |
| Sodium citrate | 0.09 |
| Methylparaben | 0.15 |
| Glycerin-substituted water-soluble silane derivative | 3 |

Both milky lotions obtained in the above-described Examples 2-3 and 2-4 were O/W emulsions, and emulsion/silica composite capsule particles were emulsified and dispersed in the outer aqueous phase.

Example 3

Transparent Gel-Form Composition

Subsequently, the present inventors prepared a glycerin-substituted water-soluble silane derivative according to the above-described synthesis example, tried the preparation of a transparent gel-form composition (facial cleanser), wherein the aforementioned water-soluble silane derivative was blended, and the appearance, texture in use, and cleansing properties were evaluated, respectively. In addition, compositions containing the same amount of silica gel particles were prepared as comparative examples, and the same evaluation was conducted. The constitutions of various compositions used for the tests and the evaluation results are both shown in Table 1. The evaluation criteria were as follows. In addition, the measurement results of small-angle X-ray diffraction for B . . . 6 or more and less than 8 panelists recognized that the texture in use was good.
C . . . 3 or more and less than 6 panelists recognized that the texture in use was good.
D . . . less than 3 panelists recognized that the texture in use was good.

Cleansing Properties

The actual usage test by 10 professional panelists was conducted for the cleansing properties when the transparent gel-form compositions of various examples and comparative examples were used. The evaluation criteria were as follows.

<Evaluation Criteria>
A . . . 8 or more panelists recognized that the cleansing properties were excellent.
B . . . 6 or more and less than 8 panelists recognized that the cleansing properties were excellent.
C . . . 3 or more and less than 6 panelists recognized that the cleansing properties were excellent.
D . . . less than 3 panelists recognized that the cleansing properties were excellent.

TABLE 1

Figure 10:
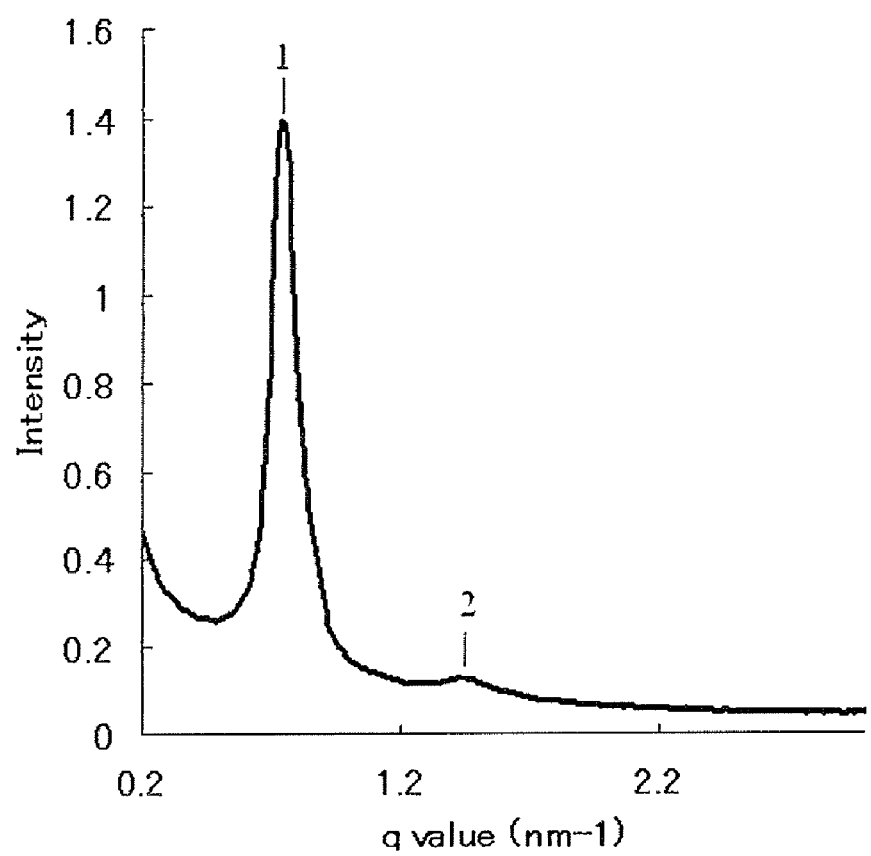
FIG. 10 shows the measurement results for small-angle X-ray diffraction analysis of the transparent gel-form cosmetic of Example 3-1.
Figure 11:
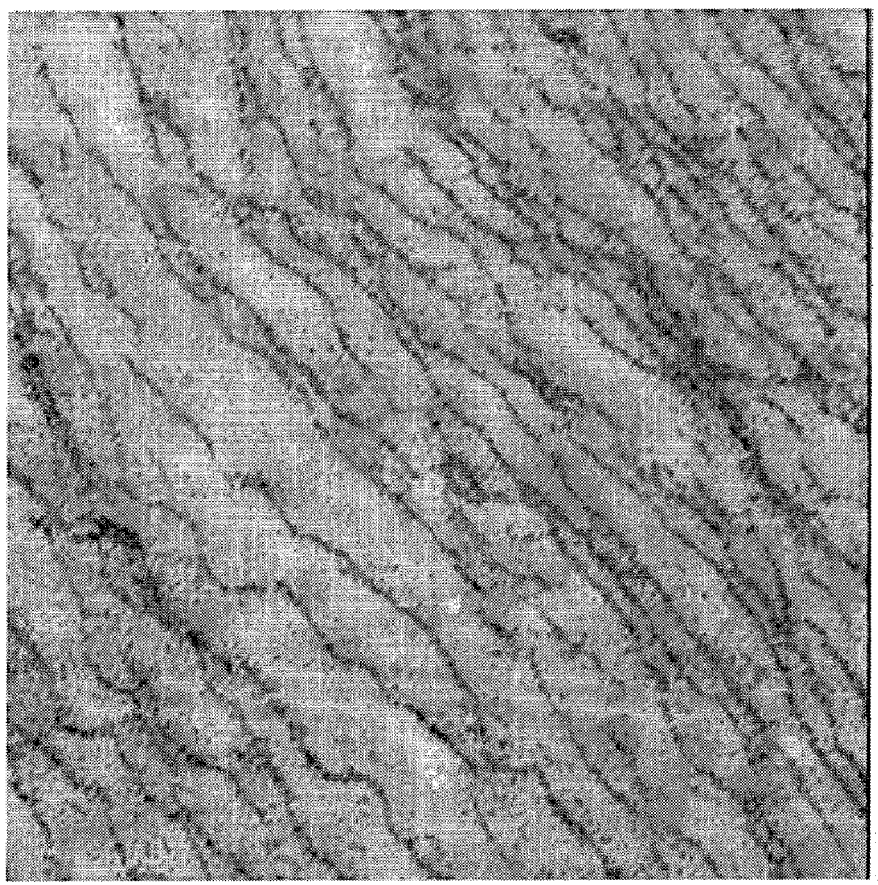
FIG. 11 shows a freeze-replica electron micrograph of the transparent gel-form cosmetic of Example 3-1.
Figure 12:
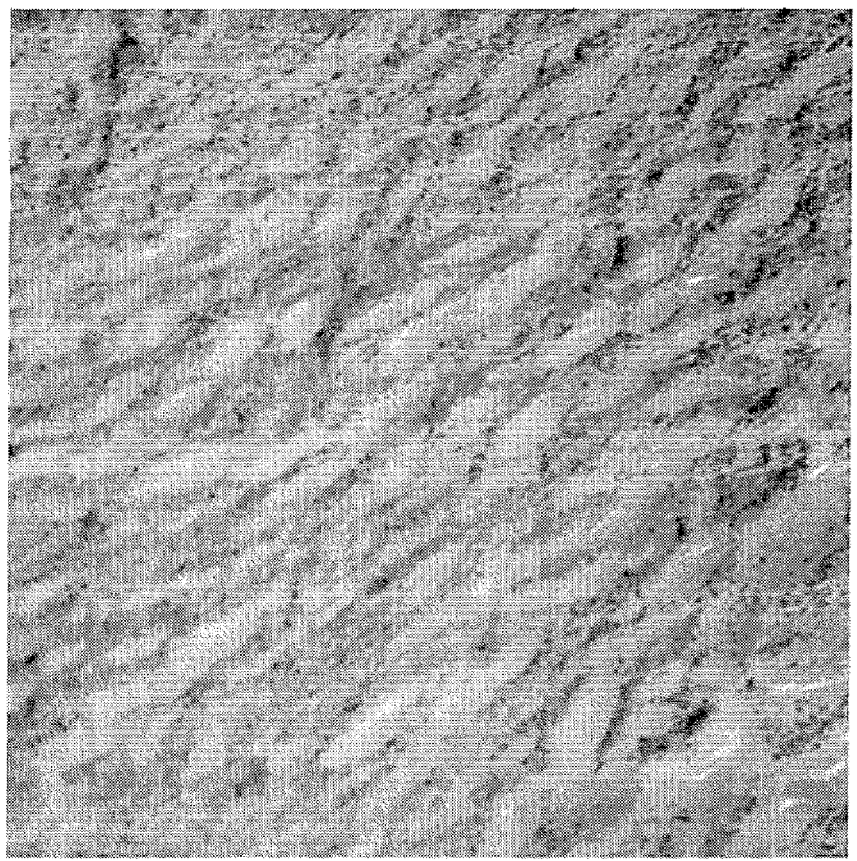
FIG. 12 shows a freeze-replica electron micrograph of the transparent gel-form cosmetic of Example 3-2.

|  | Example 3-1 | Example 3-2 | Comperative Example 3-1 | Comperative Example 3-2 | Comperative Example 3-3 | Comperative Example 3-4 |
|---|---|---|---|---|---|---|
| (A) |  |  |  |  |  |  |
| POE (8 mole) glyceryl monoisostearate | 52 | 37.5 | 52 | 37.5 | 52 | 37.5 |
| (B) |  |  |  |  |  |  |
| Decametylcyclopentasiloxane | 7.5 | 15.0 | 7.5 | 15.0 | 7.5 | 15.0 |
| Cetyl 2-ethylhexanoate | 7.5 | 15.0 | 7.5 | 15.0 | 7.5 | 15.0 |
| (C) |  |  |  |  |  |  |
| water | 18.0 | 17.6 | 18.0 | 17.6 | 18.0 | 17.6 |
| (D) |  |  |  |  |  |  |
| Glycerin-substituted water-soluble silane derivative | 10.0 | 10.0 | — | — | — | — |
| Fine particle silica | — | — | 1.52 | 1.52 | — | — |
| Glycerin | — | — | 8.48 | 8.48 | 10.0 | 10.0 |
| (E) |  |  |  |  |  |  |
| Ethanol | 5.0 | 4.9 | 5.0 | 4.9 | 5.0 | 4.9 |
| Phase | Lamellar | Bicontinuous | Separation (Precipitation) | Separation (Precipitation) | Lamellar | Bicontinuous |
| Appearance | Transparent | Transparent | Precipitation | Precipitation | Transparent | Transparent |
| Texture in use | A | A | D | D | A | B |
| Cleansing properties | A | B | D | D | C | C | the transparent gel-form composition of Example 3-1 is shown in FIG. 10. Freeze-replica electron micrographs for the transparent gel-form compositions of Examples 3-1 and 3-2 are shown in FIGS. 11 and 12, respectively.

Appearance

The appearance of the transparent gel-form compositions of various examples and comparative examples was visually evaluated.

Texture in Use

The actual usage test by 10 professional panelists was conducted for the texture in use (skin compatibility, spreadability during application, and sticky sensation) when the transparent gel-form compositions of various examples and comparative examples were used. The evaluation criteria were as follows.

<Evaluation Criteria>
A . . . 8 or more panelists recognized that the texture in use was good.

As shown in FIGS. 10 and 11, the transparent gel-form composition of Example 3-1 showed, in small-angle X-ray diffraction analysis, a sharp peak and a broad peak characteristic of a lamellar phase structure, in addition, it showed a layered structure in the freeze-replica electron micrograph. Thus, it was confirmed that a lamellar phase structure was taken. As shown in FIG. 12, it was also clarified that the transparent gel-form composition of Example 3-2 showed, in the freeze-replica electron micrograph, a structure characteristic of a bicontinuous phase.

As shown in Table 1, it was found that the transparent gel-form compositions of Examples 3-1 and 3-2 had appearance transparency and were excellent in texture in use and cleansing properties. The transparent gel-form composition with a lamellar phase structure of Example 3-1 was recognized to be excellent especially in cleansing properties. On the other hand, in the compositions of Comparative Examples 3-1 and 3-2, wherein silica gel particles and a polyhydric alcohol were blended in the same amount as the amount of the water-soluble silane derivative in Examples 3-1 and 3-2, silica particles precipitated and separated and a transparent gel-form composition was not obtained, and both texture in use and cleansing properties were extremely inferior. The compositions of Comparative Examples 3-3 and 3-4, wherein the entire amount of the water-soluble silane derivative in the compositions of Examples 3-1 and 3-2 was replaced by glycerin, were obtained as transparent gel-form compositions having a lamellar phase structure and a bicontinuous phase structure, respectively. However, they were especially inferior in cleansing properties compared with the transparent gel-form compositions of Examples 3-1 and 3-2.

Example 4

Hereinafter, the present invention will be described in further detail with reference to other examples of the transparent gel-form cosmetics of the present invention. However, the present invention is not limited by these examples.

Example 4-1

|  | (mass %) |
| --- | --- |
| POE (8 mol) glyceryl monoisostearate | 60.0 |
| Decamethylcyclopentasiloxane | 5.0 |
| Cetyl 2-ethylhexanoate | 5.0 |
| Water | 15.5 |
| Glycerin-substituted water-soluble silane derivative | 10.0 |
| Ethanol | 4.5 |

The transparent gel-form cosmetic, of Example 4-1, obtained from the above components had a lamellar phase structure, the appearance was transparent, and both texture in use and cleansing properties were excellent.

Example 4-2

|  | (mass %) |
| --- | --- |
| POE (8 mol) glyceryl monoisostearate | 50.0 |
| Decamethylcyclopentasiloxane | 5.0 |
| Cetyl 2-ethylhexanoate | 5.0 |
| Water | 24.0 |
| Glycerin-substituted water-soluble silane derivative | 10.0 |
| Ethanol | 6.0 |

The transparent gel-form cosmetic, of Example 4-2, obtained from the above components had a lamellar phase structure, the appearance was transparent, and both texture in use and cleansing properties were excellent.

Example 4-3

|  | (mass %) |
| --- | --- |
| POE (8 mol) glyceryl monoisostearate | 45.0 |
| Decamethylcyclopentasiloxane | 10.0 |
| Cetyl 2-ethylhexanoate | 10.0 |
| Water | 19.75 |
| Glycerin-substituted water-soluble silane derivative | 10.0 |
| Ethanol | 5.25 |

The transparent gel-form cosmetic, of Example 4-3, obtained from the above components had a lamellar phase structure, the appearance was transparent, and both texture in use and cleansing properties were excellent.

Example 4-4

|  | (mass %) |
| --- | --- |
| POE (8 mol) glyceryl monoisostearate | 70.0 |
| Decamethylcyclopentasiloxane | 5.0 |
| Cetyl 2-ethylhexanoate | 5.0 |
| Water | 7.0 |
| Glycerin-substituted water-soluble silane derivative | 10.0 |
| Ethanol | 3.0 |

The transparent gel-form cosmetic, of Example 4-4, obtained from the above components had a bicontinuous phase structure, the appearance was transparent, and both texture in use and cleansing properties were excellent.

Example 4-5

|  | (mass %) |
| --- | --- |
| POE (8 mol) glyceryl monoisostearate | 30.0 |
| Decamethylcyclopentasiloxane | 10.0 |
| Cetyl 2-ethylhexanoate | 10.0 |
| Water | 32.5 |
| Glycerin-substituted water-soluble silane derivative | 10.0 |
| Ethanol | 7.5 |

The transparent gel-form cosmetic, of Example 4-5, obtained from the above components had a bicontinuous phase structure, the appearance was transparent, and both texture in use and cleansing properties were excellent.

Example 4-6

|  | (mass %) |
| --- | --- |
| POE (8 mol) glyceryl monoisostearate | 30.0 |
| Decamethylcyclopentasiloxane | 25.0 |
| Cetyl 2-ethylhexanoate | 25.0 |
| Water | 7.0 |
| Glycerin-substituted water-soluble silane derivative | 10.0 |
| Ethanol | 3.0 |

The transparent gel-form cosmetic, of Example 4-6, obtained from the above components had a bicontinuous phase structure, the appearance was transparent, and both texture in use and cleansing properties were excellent.

What is claimed is:

1. A production method of an emulsion/silica composite capsule comprising the step of mixing
a surfactant except for a silane derivative, water,
an oil except for a silane derivative, and
a water-soluble silane derivative represented by the below-described general formula 1), $$Si—(OR^1)_4 \qquad (1)$$

wherein at least one $R^1$ is a polyhydric alcohol residue and the rest can be alkyl groups.

2. A transparent gel-form composition being obtained by blending a water-soluble silane derivative represented by the below-described general formula (1) into the formulation that contain
a surfactant except for the silane derivative, water, and
an oil except for the silane derivative,
and having a surfactant association structure with aqueous continuous phase or both of aqueous continuous phase and oil continuous phase in the composition, $$Si—(OR^1)_4 \qquad (1)$$

wherein at least one $R^1$ is a polyhydric alcohol residue and the rest can be alkyl groups.

3. The transparent gel-form composition according to claim 2, further comprising a water-soluble compound having hydroxyl groups in the formulation.

4. The transparent gel-form composition according to claim 2, having a lamellar phase structure or bicontinuous phase structure.

5. The transparent gel-form composition according to claim 4, having a lamellar phase structure.

6. The transparent gel-form composition according to claim 2, wherein the blending quantity of the surfactant is 20 mass % or higher of the total composition.

7. The transparent gel-form composition according to claim 2, wherein the blending ratio of the water-soluble silane derivative and the surfactant (water-soluble silane derivative/surfactant) is 0.5 or lower.

8. The transparent gel-form composition according to claim 2, wherein the surfactant is a nonionic surfactant.

9. The transparent gel-form composition according to claim 8, wherein at least one of the surfactant is a polyoxyethylene glycerin fatty acid ester.

10. The transparent gel-form composition according to claim 2, wherein at least one of the oil component is a silicone oil.

11. The transparent gel-form composition according to claim 3, wherein at least one of the water-soluble compound having hydroxyl groups is ethanol, glycerin, or 1,3-butylene glycol.

12. A transparent gel-form cosmetic consisting of the transparent gel-form composition according to claim 2.

13. A transparent gel-form cleanser consisting of the transparent gel-form composition according to claim 2.

14. A production method of the transparent gel-form composition comprising the step of blending a water-soluble silane derivative represented by the below-described general formula (1) into the formulation that contains
a surfactant except for the silane derivative,
an oil except for the silane derivative, and water, and capable of taking a surfactant association structure with aqueous continuous phase or both of aqueous continuous phase and oil continuous phase in the formulation, $$Si—(OR^1)_4 \qquad (1)$$

wherein at least one $R^1$ is a polyhydric alcohol residue and the rest can be alkyl groups.

15. The production method of an emulsion/silica composite capsule according to claim 1, wherein the $R^1$ in general formula (I) is a polyhydric alcohol residue selected from the group consisted of an ethylene glycol residue, a diethylene glycol residue, a triethylene glycol residue, a tetraethylene glycol residue, a polyethylene glycol residue, a propylene glycol residue, a dipropylene glycol residue, a polypropylene glycol residue, a butylene glycol residue, a hexylene glycol residue, a glycerin residue, a diglycerin residue, a polyglycerin residue, a neopentyl glycol residue, a trimethylolpropane residue, a pentaerythritol residue, and a maltitol residue.

16. The production method of an emulsion/silica composite capsule according to claim 1, wherein the water-soluble silane derivative is one selected from the group consisted of Si—(O—CH$_2$—CH$_2$—OH)$_4$, Si—(O—CH$_2$—CH$_2$-CH$_2$—OH)$_4$, Si—(O—CH$_2$—CH$_2$—CHOH—CH$_3$)$_4$, and Si—(O—CH$_2$—CHOH—CH$_2$—OH)$_4$.

17. The transparent gel-form composition according to claim 2, wherein the $R^1$ in general formula (1) is a polyhydric alcohol residue selected from the group consisted of an ethylene glycol residue, a diethylene glycol residue, a triethylene glycol residue, a tetraethylene glycol residue, a polyethylene glycol residue, a propylene glycol residue, a dipropylene glycol residue, a polypropylene glycol residue, a butylene glycol residue, a hexylene glycol residue, a glycerin residue, a diglycerin residue, a polyglycerin residue, a neopentyl glycol residue, a trimethylolpropane residue, a pentaerythritol residue, and a maltitol residue.

18. The transparent gel-form composition according to claim 2, wherein the water-soluble silane derivative is one selected from the group consisted of Si—(O—CH$_2$—CH$_2$—OH)$_4$, Si—(O—CH$_2$—CH$_2$—CH$_2$—OH)$_4$, Si—(O—CH$_2$—CH$_2$—CHOH—CH$_3$)$_4$, and Si—(O—CH$_2$—CHOH—CH$_2$—OH)$_4$.

19. The production method of the transparent gel-form composition according to claim 14, wherein the $R^1$ in general formula (1) is a polyhydric alcohol residue selected from the group consisted of an ethylene glycol residue, a diethylene glycol residue, a triethylene glycol residue, a tetraethylene glycol residue, a polyethylene glycol residue, a propylene glycol residue, a dipropylene glycol residue, a polypropylene glycol residue, a butylene glycol residue, a hexylene glycol residue, a glycerin residue, a diglycerin residue, a polyglycerin residue, a neopentyl glycol residue, a trimethylolpropane residue, a pentaerythritol residue, and a maltitol residue.

20. The production method of the transparent gel-form composition according to claim 14, wherein the water-soluble silane derivative is one selected from the group consisted of Si—(O—CH$_2$—CH$_2$—OH)$_4$, Si—(O—CH$_2$—CH$_2$—CH$_2$—OH)$_4$, Si—(O—CH$_2$—CH$_2$—CHOH—CH$_3$)$_4$, and Si—(O—CH$_2$—CHOH—CH$_2$—OH)$_4$.

* * * * *